United States Patent
Lamego et al.

(10) Patent No.: US 11,367,529 B2
(45) Date of Patent: Jun. 21, 2022

(54) PHYSIOLOGICAL TEST CREDIT METHOD

(71) Applicant: Cercacor Laboratories, Inc., Irvine, CA (US)

(72) Inventors: Marcelo M. Lamego, Coto De Caza, CA (US); Jeroen Poeze, Mission Viejo, CA (US)

(73) Assignee: Cercacor Laboratories, Inc., Irvine, CA (US)

( * ) Notice: Subject to any disclaimer, the term of this patent is extended or adjusted under 35 U.S.C. 154(b) by 0 days.

(21) Appl. No.: 17/125,713

(22) Filed: Dec. 17, 2020

(65) Prior Publication Data

US 2021/0217520 A1 Jul. 15, 2021

Related U.S. Application Data

(63) Continuation of application No. 16/383,380, filed on Apr. 12, 2019, now abandoned, which is a
(Continued)

(51) Int. Cl.
*G06Q 20/14* (2012.01)
*A61B 5/00* (2006.01)
(Continued)

(52) U.S. Cl.
CPC ........... *G16H 40/67* (2018.01); *A61B 5/0002* (2013.01); *G06Q 20/145* (2013.01); *H04L 43/16* (2013.01);
(Continued)

(58) Field of Classification Search
CPC ............. G06Q 20/08–18; G06Q 20/28; G16H 40/60–67; G06F 19/34–3418; G06F 21/00–88; A61B 5/0002–0024
See application file for complete search history.

(56) References Cited

U.S. PATENT DOCUMENTS

| 4,815,469 A | 3/1989 | Cohen et al. |
| 4,858,615 A | 8/1989 | Meinema |

(Continued)

FOREIGN PATENT DOCUMENTS

| JP | H08-315919 | 11/1996 |
| JP | H11-156657 | 11/1997 |

(Continued)

OTHER PUBLICATIONS

US 8,845,543 B2, 09/2014, Diab et al. (withdrawn)
(Continued)

*Primary Examiner* — David R Lazaro
*Assistant Examiner* — Julian Chang
(74) *Attorney, Agent, or Firm* — Knobbe, Martens, Olson & Bear, LLP

(57) ABSTRACT

A physiological test credit method determines if test credits are available to the monitor and checks if a Wi-Fi connection is available. If test credits are less than a test credit threshold, the monitor connects to a test credit server, processes server commands so as to download test credits and disconnects from the server. In various embodiments, the monitor is challenged to break a server code, the server is challenged to break a monitor code. The server validates monitor serial codes, and saves monitor configuration parameters.

20 Claims, 7 Drawing Sheets

Related U.S. Application Data continuation of application No. 15/713,275, filed on Sep. 22, 2017, now Pat. No. 10,305,775, which is a continuation of application No. 14/071,447, filed on Nov. 4, 2013, now Pat. No. 9,787,568.

(60) Provisional application No. 61/722,245, filed on Nov. 5, 2012.

(51) Int. Cl.
    *G16H 40/67*     (2018.01)
    *H04L 43/16*     (2022.01)
    *A61B 5/1455*    (2006.01)

(52) U.S. Cl.
    CPC ..... *A61B 5/14551* (2013.01); *A61B 2560/028* (2013.01)

(56) References Cited

U.S. PATENT DOCUMENTS

| | | | |
|---|---|---|---|
| 4,900,904 | A * | 2/1990 | Wright ............... G06K 7/0034 235/380 |
| 4,960,128 | A | 10/1990 | Gordon et al. |
| 4,964,408 | A | 10/1990 | Hink et al. |
| 5,041,187 | A | 8/1991 | Hink et al. |
| 5,069,213 | A | 12/1991 | Hink et al. |
| 5,163,438 | A | 11/1992 | Gordon et al. |
| 5,317,269 | A | 5/1994 | Mills et al. |
| 5,319,355 | A | 6/1994 | Russek |
| 5,337,744 | A | 8/1994 | Branigan |
| 5,341,805 | A | 8/1994 | Stavridi et al. |
| D353,195 | S | 12/1994 | Savage et al. |
| D353,196 | S | 12/1994 | Savage et al. |
| 5,377,676 | A | 1/1995 | Vari et al. |
| D359,546 | S | 6/1995 | Savage et al. |
| 5,431,170 | A | 7/1995 | Mathews |
| 5,436,499 | A | 7/1995 | Namavar et al. |
| D361,840 | S | 8/1995 | Savage et al. |
| D362,063 | S | 9/1995 | Savage et al. |
| 5,452,717 | A | 9/1995 | Branigan et al. |
| D363,120 | S | 10/1995 | Savage et al. |
| 5,456,252 | A | 10/1995 | Vari et al. |
| 5,479,934 | A | 1/1996 | Imran |
| 5,482,036 | A | 1/1996 | Diab et al. |
| 5,490,505 | A | 2/1996 | Diab et al. |
| 5,494,043 | A | 2/1996 | O'Sullivan et al. |
| 5,533,511 | A | 7/1996 | Kaspar et al. |
| 5,534,851 | A | 7/1996 | Russek |
| 5,561,275 | A | 10/1996 | Savage et al. |
| 5,562,002 | A | 10/1996 | Lalin |
| 5,590,649 | A | 1/1997 | Caro et al. |
| 5,602,924 | A | 2/1997 | Durand et al. |
| 5,632,272 | A | 5/1997 | Diab et al. |
| 5,638,816 | A | 6/1997 | Kiani-Azarbayjany et al. |
| 5,638,818 | A | 6/1997 | Diab et al. |
| 5,645,440 | A | 7/1997 | Tobler et al. |
| 5,671,914 | A | 9/1997 | Kalkhoran et al. |
| 5,685,299 | A | 11/1997 | Diab et al. |
| 5,726,440 | A | 3/1998 | Kalkhoran et al. |
| D393,830 | S | 4/1998 | Tobler et al. |
| 5,743,262 | A | 4/1998 | Lepper, Jr. et al. |
| 5,747,806 | A | 5/1998 | Khalil et al. |
| 5,750,994 | A | 5/1998 | Schlager |
| 5,758,644 | A | 6/1998 | Diab et al. |
| 5,760,910 | A | 6/1998 | Lepper, Jr. et al. |
| 5,769,785 | A | 6/1998 | Diab et al. |
| 5,782,757 | A | 7/1998 | Diab et al. |
| 5,785,659 | A | 7/1998 | Caro et al. |
| 5,791,347 | A | 8/1998 | Flaherty et al. |
| 5,810,734 | A | 9/1998 | Caro et al. |
| 5,823,950 | A | 10/1998 | Diab et al. |
| 5,830,131 | A | 11/1998 | Caro et al. |
| 5,833,618 | A | 11/1998 | Caro et al. |
| 5,860,919 | A | 1/1999 | Kiani-Azarbayjany et al. |
| 5,890,929 | A | 4/1999 | Mills et al. |
| 5,904,654 | A | 5/1999 | Wohltmann et al. |
| 5,919,134 | A | 7/1999 | Diab |
| 5,934,925 | A | 8/1999 | Tobler et al. |
| 5,940,182 | A | 8/1999 | Lepper, Jr. et al. |
| 5,963,915 | A | 10/1999 | Kirsch |
| 5,987,343 | A | 11/1999 | Kinast |
| 5,991,355 | A | 11/1999 | Dahlke |
| 5,995,855 | A | 11/1999 | Kiani et al. |
| 5,997,343 | A | 12/1999 | Mills et al. |
| 6,002,952 | A | 12/1999 | Diab et al. |
| 6,010,937 | A | 1/2000 | Karam et al. |
| 6,011,986 | A | 1/2000 | Diab et al. |
| 6,027,452 | A | 2/2000 | Flaherty et al. |
| 6,036,642 | A | 3/2000 | Diab et al. |
| 6,040,578 | A | 3/2000 | Malin et al. |
| 6,045,509 | A | 4/2000 | Caro et al. |
| 6,066,204 | A | 5/2000 | Haven |
| 6,067,462 | A | 5/2000 | Diab et al. |
| 6,069,955 | A * | 5/2000 | Coppersmith ....... G06Q 10/087 380/200 |
| 6,081,735 | A | 6/2000 | Diab et al. |
| 6,088,607 | A | 7/2000 | Diab et al. |
| 6,108,789 | A * | 8/2000 | Dancs ................ G06Q 20/3552 713/168 |
| 6,110,522 | A | 8/2000 | Lepper, Jr. et al. |
| 6,112,305 | A * | 8/2000 | Dancs .................. H04L 9/3268 713/168 |
| 6,115,673 | A | 9/2000 | Malin et al. |
| 6,124,597 | A | 9/2000 | Shehada et al. |
| 6,128,521 | A | 10/2000 | Marro et al. |
| 6,129,675 | A | 10/2000 | Jay |
| 6,141,752 | A * | 10/2000 | Dancs ................ H04L 63/0853 380/255 |
| 6,144,868 | A | 11/2000 | Parker |
| 6,151,516 | A | 11/2000 | Kiani-Azarbayjany et al. |
| 6,152,754 | A | 11/2000 | Gerhardt et al. |
| 6,157,850 | A | 12/2000 | Diab et al. |
| 6,165,005 | A | 12/2000 | Mills et al. |
| 6,184,521 | B1 | 2/2001 | Coffin, IV et al. |
| 6,206,830 | B1 | 3/2001 | Diab et al. |
| 6,229,856 | B1 | 5/2001 | Diab et al. |
| 6,232,609 | B1 | 5/2001 | Snyder et al. |
| 6,236,872 | B1 | 5/2001 | Diab et al. |
| 6,241,683 | B1 | 6/2001 | Macklem et al. |
| 6,253,097 | B1 | 6/2001 | Aronow et al. |
| 6,255,708 | B1 | 7/2001 | Sudharsanan et al. |
| 6,256,523 | B1 | 7/2001 | Diab et al. |
| 6,263,222 | B1 | 7/2001 | Diab et al. |
| 6,278,522 | B1 | 8/2001 | Lepper, Jr. et al. |
| 6,280,213 | B1 | 8/2001 | Tobler et al. |
| 6,280,381 | B1 | 8/2001 | Malin et al. |
| 6,285,896 | B1 | 9/2001 | Tobler et al. |
| 6,301,493 | B1 | 10/2001 | Marro et al. |
| 6,308,089 | B1 | 10/2001 | von der Ruhr et al. |
| 6,317,627 | B1 | 11/2001 | Ennen et al. |
| 6,321,100 | B1 | 11/2001 | Parker |
| 6,325,761 | B1 | 12/2001 | Jay |
| 6,330,468 | B1 | 12/2001 | Scharf |
| 6,334,065 | B1 | 12/2001 | Al-Ali et al. |
| 6,343,224 | B1 | 1/2002 | Parker |
| 6,349,228 | B1 | 2/2002 | Kiani et al. |
| 6,360,114 | B1 | 3/2002 | Diab et al. |
| 6,368,283 | B1 | 4/2002 | Xu et al. |
| 6,371,921 | B1 | 4/2002 | Caro et al. |
| 6,377,829 | B1 | 4/2002 | Al-Ali |
| 6,388,240 | B2 | 5/2002 | Schulz et al. |
| 6,397,091 | B2 | 5/2002 | Diab et al. |
| 6,411,373 | B1 | 6/2002 | Garside et al. |
| 6,415,167 | B1 | 7/2002 | Blank et al. |
| 6,419,636 | B1 | 7/2002 | Young et al. |
| 6,430,437 | B1 | 8/2002 | Marro |
| 6,430,525 | B1 | 8/2002 | Weber et al. |
| 6,433,696 | B1 | 8/2002 | Deiterman et al. |
| 6,463,310 | B1 | 10/2002 | Swedlow et al. |
| 6,463,311 | B1 | 10/2002 | Diab |
| 6,470,199 | B1 | 10/2002 | Kopotic et al. |
| 6,487,429 | B2 | 11/2002 | Hockersmith et al. |
| 6,499,843 | B1 | 12/2002 | Cox et al. |

(56) References Cited

U.S. PATENT DOCUMENTS

| | | |
|---|---|---|
| 6,501,975 B2 | 12/2002 | Diab et al. |
| 6,505,059 B1 | 1/2003 | Kollias et al. |
| 6,515,273 B2 | 2/2003 | Al-Ali |
| 6,519,487 B1 | 2/2003 | Parker |
| 6,525,386 B1 | 2/2003 | Mills et al. |
| 6,526,300 B1 | 2/2003 | Kiani et al. |
| 6,534,012 B1 | 3/2003 | Hazen et al. |
| 6,541,756 B2 | 4/2003 | Schulz et al. |
| 6,542,764 B1 | 4/2003 | Al-Ali et al. |
| 6,553,241 B2 | 4/2003 | Mannheimer et al. |
| 6,580,086 B1 | 6/2003 | Schulz et al. |
| 6,584,336 B1 | 6/2003 | Ali et al. |
| 6,587,196 B1 | 7/2003 | Stippick et al. |
| 6,587,199 B1 | 7/2003 | Luu |
| 6,587,945 B1 | 7/2003 | Pasieka |
| 6,595,316 B2 | 7/2003 | Cybulski et al. |
| 6,597,932 B2 | 7/2003 | Tian et al. |
| 6,597,933 B2 | 7/2003 | Kiani et al. |
| 6,606,511 B1 | 8/2003 | Ali et al. |
| 6,631,353 B1 | 10/2003 | Davis et al. |
| 6,632,181 B2 | 10/2003 | Flaherty et al. |
| 6,635,559 B2 | 10/2003 | Greenwald et al. |
| 6,639,668 B1 | 10/2003 | Trepagnier |
| 6,640,116 B2 | 10/2003 | Diab |
| 6,640,117 B2 | 10/2003 | Makarewicz et al. |
| 6,643,530 B2 | 11/2003 | Diab et al. |
| 6,650,917 B2 | 11/2003 | Diab et al. |
| 6,654,624 B2 | 11/2003 | Diab et al. |
| 6,658,276 B2 | 12/2003 | Kiani et al. |
| 6,661,161 B1 | 12/2003 | Lanzo et al. |
| 6,671,531 B2 | 12/2003 | Al-Ali |
| 6,678,543 B2 | 1/2004 | Diab et al. |
| 6,684,090 B2 | 1/2004 | Ali et al. |
| 6,684,091 B2 | 1/2004 | Parker |
| 6,697,656 B1 | 2/2004 | Al-Ali |
| 6,697,657 B1 | 2/2004 | Shehada et al. |
| 6,697,658 B2 | 2/2004 | Al-Ali |
| RE38,476 E | 3/2004 | Diab et al. |
| 6,699,194 B1 | 3/2004 | Diab et al. |
| 6,704,786 B1 * | 3/2004 | Gupta .................. H04L 69/16 709/227 |
| 6,714,804 B2 | 3/2004 | Al-Ali et al. |
| RE38,492 E | 4/2004 | Diab et al. |
| 6,721,582 B2 | 4/2004 | Trepagnier et al. |
| 6,721,585 B1 | 4/2004 | Parker |
| 6,725,075 B2 | 4/2004 | Al-Ali |
| 6,728,560 B2 | 4/2004 | Kollias et al. |
| 6,735,459 B2 | 5/2004 | Parker |
| 6,738,652 B2 | 5/2004 | Mattu et al. |
| 6,745,060 B2 | 6/2004 | Diab et al. |
| 6,760,607 B2 | 7/2004 | Al-Ali |
| 6,770,028 B1 | 8/2004 | Ali et al. |
| 6,771,994 B2 | 8/2004 | Kiani et al. |
| 6,775,782 B1 | 8/2004 | Buros et al. |
| 6,788,965 B2 | 9/2004 | Ruchti et al. |
| 6,792,300 B1 | 9/2004 | Diab et al. |
| 6,813,511 B2 | 11/2004 | Diab et al. |
| 6,816,241 B2 | 11/2004 | Grubisic |
| 6,816,741 B2 | 11/2004 | Diab |
| 6,822,564 B2 | 11/2004 | Al-Ali |
| 6,826,419 B2 | 11/2004 | Diab et al. |
| 6,830,711 B2 | 12/2004 | Mills et al. |
| 6,836,765 B1 | 12/2004 | Sussman |
| 6,850,787 B2 | 2/2005 | Weber et al. |
| 6,850,788 B2 | 2/2005 | Al-Ali |
| 6,852,083 B2 | 2/2005 | Caro et al. |
| 6,861,639 B2 | 3/2005 | Al-Ali |
| 6,876,931 B2 | 4/2005 | Lorenz et al. |
| 6,898,452 B2 | 5/2005 | Al-Ali et al. |
| 6,920,345 B2 | 7/2005 | Al-Ali et al. |
| 6,931,268 B1 | 8/2005 | Kiani-Azarbayjany et al. |
| 6,934,570 B2 | 8/2005 | Kiani et al. |
| 6,939,305 B2 | 9/2005 | Flaherty et al. |
| 6,943,348 B1 | 9/2005 | Coffin IV |
| 6,950,687 B2 | 9/2005 | Al-Ali |
| 6,956,649 B2 | 10/2005 | Acosta et al. |
| 6,961,598 B2 | 11/2005 | Diab |
| 6,970,792 B1 | 11/2005 | Diab |
| 6,979,812 B2 | 12/2005 | Al-Ali |
| 6,985,764 B2 | 1/2006 | Mason et al. |
| 6,990,364 B2 | 1/2006 | Ruchti et al. |
| 6,993,371 B2 | 1/2006 | Kiani et al. |
| 6,996,427 B2 | 2/2006 | Ali et al. |
| 6,997,879 B1 | 2/2006 | Turcott |
| 6,998,247 B2 | 2/2006 | Monfre et al. |
| 6,999,904 B2 | 2/2006 | Weber et al. |
| 7,003,338 B2 | 2/2006 | Weber et al. |
| 7,003,339 B2 | 2/2006 | Diab et al. |
| 7,015,451 B2 | 3/2006 | Dalke et al. |
| 7,024,233 B2 | 4/2006 | Ali et al. |
| 7,027,849 B2 | 4/2006 | Al-Ali |
| 7,030,749 B2 | 4/2006 | Al-Ali |
| 7,039,449 B2 | 5/2006 | Al-Ali |
| 7,041,060 B2 | 5/2006 | Flaherty et al. |
| 7,044,918 B2 | 5/2006 | Diab |
| 7,067,893 B2 | 6/2006 | Mills et al. |
| D526,719 S | 8/2006 | Richie, Jr. et al. |
| 7,096,052 B2 | 8/2006 | Mason et al. |
| 7,096,054 B2 | 8/2006 | Abdul-Hafiz et al. |
| D529,616 S | 10/2006 | Deros et al. |
| 7,132,641 B2 | 11/2006 | Schulz et al. |
| 7,133,710 B2 | 11/2006 | Acosta et al. |
| 7,142,901 B2 | 11/2006 | Kiani et al. |
| 7,149,561 B2 | 12/2006 | Diab |
| 7,186,966 B2 | 3/2007 | Al-Ali |
| 7,190,261 B2 | 3/2007 | Al-Ali |
| 7,215,984 B2 | 5/2007 | Diab et al. |
| 7,215,986 B2 | 5/2007 | Diab et al. |
| 7,221,971 B2 | 5/2007 | Diab et al. |
| 7,225,006 B2 | 5/2007 | Al-Ali et al. |
| 7,225,007 B2 | 5/2007 | Al-Ali et al. |
| RE39,672 E | 6/2007 | Shehada et al. |
| 7,239,905 B2 | 7/2007 | Kiani-Azarbayjany et al. |
| 7,245,953 B1 | 7/2007 | Parker |
| 7,254,429 B2 | 8/2007 | Schurman et al. |
| 7,254,431 B2 | 8/2007 | Al-Ali et al. |
| 7,254,433 B2 | 8/2007 | Diab et al. |
| 7,254,434 B2 | 8/2007 | Schulz et al. |
| 7,272,425 B2 | 9/2007 | Al-Ali |
| 7,274,955 B2 | 9/2007 | Kiani et al. |
| D554,263 S | 10/2007 | Al-Ali et al. |
| 7,280,858 B2 | 10/2007 | Al-Ali et al. |
| 7,289,835 B2 | 10/2007 | Mansfield et al. |
| 7,292,883 B2 | 11/2007 | De Felice et al. |
| 7,295,866 B2 | 11/2007 | Al-Ali |
| 7,328,053 B1 | 2/2008 | Diab et al. |
| 7,332,784 B2 | 2/2008 | Mills et al. |
| 7,340,287 B2 | 3/2008 | Mason et al. |
| 7,341,559 B2 | 3/2008 | Schulz et al. |
| 7,343,186 B2 | 3/2008 | Lamego et al. |
| 7,349,856 B2 | 3/2008 | Ackermann et al. |
| D566,282 S | 4/2008 | Al-Ali et al. |
| 7,355,512 B1 | 4/2008 | Al-Ali |
| 7,356,365 B2 | 4/2008 | Schurman |
| 7,371,981 B2 | 5/2008 | Abdul-Hafiz |
| 7,373,193 B2 | 5/2008 | Al-Ali et al. |
| 7,373,194 B2 | 5/2008 | Weber et al. |
| 7,376,453 B1 | 5/2008 | Diab et al. |
| 7,377,794 B2 | 5/2008 | Al-Ali et al. |
| 7,377,899 B2 | 5/2008 | Weber et al. |
| 7,383,070 B2 | 6/2008 | Diab et al. |
| 7,390,299 B2 | 6/2008 | Weiner et al. |
| 7,394,370 B2 | 7/2008 | Chan |
| 7,395,158 B2 | 7/2008 | Monfre et al. |
| 7,415,297 B2 | 8/2008 | Al-Ali et al. |
| 7,428,432 B2 | 9/2008 | Ali et al. |
| 7,438,683 B2 | 10/2008 | Al-Ali et al. |
| 7,440,787 B2 | 10/2008 | Diab |
| 7,444,436 B2 | 10/2008 | Wille |
| 7,450,927 B1 * | 11/2008 | Creswell ................. H04L 12/14 455/405 |
| 7,454,240 B2 | 11/2008 | Diab et al. |
| 7,467,002 B2 | 12/2008 | Weber et al. |
| 7,469,157 B2 | 12/2008 | Diab et al. |

(56) References Cited

U.S. PATENT DOCUMENTS

| | | | |
|---|---|---|---|
| 7,471,969 B2 | 12/2008 | Diab et al. | |
| 7,471,971 B2 | 12/2008 | Diab et al. | |
| 7,483,729 B2 | 1/2009 | Al-Ali et al. | |
| 7,483,730 B2 | 1/2009 | Diab et al. | |
| 7,489,958 B2 | 2/2009 | Diab et al. | |
| 7,496,391 B2 | 2/2009 | Diab et al. | |
| 7,496,393 B2 | 2/2009 | Diab et al. | |
| D587,657 S | 3/2009 | Al-Ali et al. | |
| 7,499,741 B2 | 3/2009 | Diab et al. | |
| 7,499,835 B2 | 3/2009 | Weber et al. | |
| 7,500,950 B2 | 3/2009 | Al-Ali et al. | |
| 7,509,154 B2 | 3/2009 | Diab et al. | |
| 7,509,494 B2 | 3/2009 | Al-Ali | |
| 7,510,849 B2 | 3/2009 | Schurman et al. | |
| 7,514,725 B2 | 4/2009 | Wojtczuk et al. | |
| 7,519,406 B2 | 4/2009 | Blank et al. | |
| 7,520,430 B1 | 4/2009 | Stewart et al. | |
| 7,526,328 B2 | 4/2009 | Diab et al. | |
| D592,507 S | 5/2009 | Wachman et al. | |
| 7,530,942 B1 | 5/2009 | Diab | |
| 7,530,949 B2 | 5/2009 | Al Ali et al. | |
| 7,530,955 B2 | 5/2009 | Diab et al. | |
| 7,563,110 B2 | 7/2009 | Al-Ali et al. | |
| 7,571,265 B2 * | 8/2009 | Thacker | G06F 21/71 710/36 |
| 7,593,230 B2 | 9/2009 | Abul-Haj et al. | |
| 7,596,398 B2 | 9/2009 | Al-Ali et al. | |
| 7,606,608 B2 | 10/2009 | Blank et al. | |
| 7,618,375 B2 | 11/2009 | Flaherty et al. | |
| 7,620,674 B2 | 11/2009 | Ruchti et al. | |
| D606,659 S | 12/2009 | Kiani et al. | |
| 7,629,039 B2 | 12/2009 | Eckerbom et al. | |
| 7,640,140 B2 | 12/2009 | Ruchti et al. | |
| 7,647,083 B2 | 1/2010 | Al-Ali et al. | |
| D609,193 S | 2/2010 | Al-Ali et al. | |
| 7,660,616 B1 | 2/2010 | Poore | |
| D614,305 S | 4/2010 | Al-Ali et al. | |
| 7,697,966 B2 | 4/2010 | Monfre et al. | |
| 7,698,105 B2 | 4/2010 | Ruchti et al. | |
| RE41,317 E | 5/2010 | Parker | |
| RE41,333 E | 5/2010 | Blank et al. | |
| 7,711,612 B1 * | 5/2010 | Farias | G06Q 10/087 705/28 |
| 7,729,733 B2 | 6/2010 | Al-Ali et al. | |
| 7,734,320 B2 | 6/2010 | Al-Ali | |
| 7,761,127 B2 | 7/2010 | Al-Ali et al. | |
| 7,761,128 B2 | 7/2010 | Al-Ali et al. | |
| 7,764,982 B2 | 7/2010 | Dalke et al. | |
| D621,516 S | 8/2010 | Kiani et al. | |
| 7,791,155 B2 | 9/2010 | Diab | |
| 7,797,248 B1 * | 9/2010 | Bierbaum | G06Q 20/0652 705/1.1 |
| 7,801,581 B2 | 9/2010 | Diab | |
| 7,822,452 B2 | 10/2010 | Schurman et al. | |
| RE41,912 E | 11/2010 | Parker | |
| 7,844,313 B2 | 11/2010 | Kiani et al. | |
| 7,844,314 B2 | 11/2010 | Al-Ali | |
| 7,844,315 B2 | 11/2010 | Al-Ali | |
| 7,865,222 B2 | 1/2011 | Weber et al. | |
| 7,873,497 B2 | 1/2011 | Weber et al. | |
| 7,880,606 B2 | 2/2011 | Al-Ali | |
| 7,880,626 B2 | 2/2011 | Al-Ali et al. | |
| 7,881,761 B2 | 2/2011 | Mannheimer et al. | |
| 7,891,355 B2 | 2/2011 | Al-Ali et al. | |
| 7,894,868 B2 | 2/2011 | Al-Ali et al. | |
| 7,899,507 B2 | 3/2011 | Al-Ali et al. | |
| 7,899,518 B2 | 3/2011 | Trepagnier et al. | |
| 7,904,132 B2 | 3/2011 | Weber et al. | |
| 7,909,772 B2 | 3/2011 | Popov et al. | |
| 7,910,875 B2 | 3/2011 | Al-Ali | |
| 7,919,713 B2 | 4/2011 | Al-Ali et al. | |
| 7,937,128 B2 | 5/2011 | Al-Ali | |
| 7,937,129 B2 | 5/2011 | Mason et al. | |
| 7,937,130 B2 | 5/2011 | Diab et al. | |
| 7,941,199 B2 | 5/2011 | Kiani | |
| 7,951,086 B2 | 5/2011 | Flaherty et al. | |
| 7,957,780 B2 | 6/2011 | Lamego et al. | |
| 7,962,188 B2 | 6/2011 | Kiani et al. | |
| 7,962,190 B1 | 6/2011 | Diab et al. | |
| 7,976,472 B2 | 7/2011 | Kiani | |
| 7,988,637 B2 | 8/2011 | Diab | |
| 7,990,382 B2 | 8/2011 | Kiani | |
| 7,991,446 B2 | 8/2011 | Ali et al. | |
| 8,000,761 B2 | 8/2011 | Al-Ali | |
| 8,008,088 B2 | 8/2011 | Bellott et al. | |
| RE42,753 E | 9/2011 | Kiani-Azarbayjany et al. | |
| 8,019,400 B2 | 9/2011 | Diab et al. | |
| 8,028,701 B2 | 10/2011 | Al-Ali et al. | |
| 8,029,765 B2 | 10/2011 | Bellott et al. | |
| 8,036,727 B2 | 10/2011 | Schurman et al. | |
| 8,036,728 B2 | 10/2011 | Diab et al. | |
| 8,046,040 B2 | 10/2011 | Ali et al. | |
| 8,046,041 B2 | 10/2011 | Diab et al. | |
| 8,046,042 B2 | 10/2011 | Diab et al. | |
| 8,048,040 B2 | 11/2011 | Kiani | |
| 8,050,728 B2 | 11/2011 | Al-Ali et al. | |
| RE43,169 E | 2/2012 | Parker | |
| 8,118,620 B2 | 2/2012 | Al-Ali et al. | |
| 8,126,528 B2 | 2/2012 | Diab et al. | |
| 8,128,572 B2 | 3/2012 | Diab et al. | |
| 8,130,105 B2 | 3/2012 | Al-Ali et al. | |
| 8,145,287 B2 | 3/2012 | Diab et al. | |
| 8,150,487 B2 | 4/2012 | Diab et al. | |
| D659,836 S | 5/2012 | Bensch et al. | |
| 8,175,672 B2 | 5/2012 | Parker | |
| 8,180,420 B2 | 5/2012 | Diab et al. | |
| 8,182,443 B1 | 5/2012 | Kiani | |
| 8,185,180 B2 | 5/2012 | Diab et al. | |
| 8,190,223 B2 | 5/2012 | Al-Ali et al. | |
| 8,190,227 B2 | 5/2012 | Diab et al. | |
| 8,203,438 B2 | 6/2012 | Kiani et al. | |
| 8,203,704 B2 | 6/2012 | Merritt et al. | |
| 8,204,566 B2 | 6/2012 | Schurman et al. | |
| D663,421 S | 7/2012 | Steiner et al. | |
| 8,219,172 B2 | 7/2012 | Schurman et al. | |
| 8,222,166 B2 | 7/2012 | Chu et al. | |
| 8,224,411 B2 | 7/2012 | Al-Ali et al. | |
| 8,228,181 B2 | 7/2012 | Al-Ali | |
| 8,229,532 B2 | 7/2012 | Davis | |
| 8,229,533 B2 | 7/2012 | Diab et al. | |
| 8,233,955 B2 | 7/2012 | Al-Ali et al. | |
| 8,234,126 B1 * | 7/2012 | Estes | G06F 19/3468 705/2 |
| 8,244,325 B2 | 8/2012 | Al-Ali et al. | |
| 8,255,026 B1 | 8/2012 | Al-Ali | |
| 8,255,027 B2 | 8/2012 | Al-Ali et al. | |
| 8,255,028 B2 | 8/2012 | Al-Ali et al. | |
| 8,260,577 B2 | 9/2012 | Weber et al. | |
| 8,265,723 B1 | 9/2012 | McHale et al. | |
| 8,274,360 B2 | 9/2012 | Sampath et al. | |
| 8,280,473 B2 | 10/2012 | Al-Ali | |
| 8,294,747 B1 * | 10/2012 | Weinberg | H04N 7/148 348/14.02 |
| 8,301,217 B2 | 10/2012 | Al-Ali et al. | |
| 8,306,596 B2 | 11/2012 | Schurman et al. | |
| 8,310,336 B2 | 11/2012 | Muhsin et al. | |
| 8,315,683 B2 | 11/2012 | Al-Ali et al. | |
| RE43,860 E | 12/2012 | Parker | |
| 8,337,403 B2 | 12/2012 | Al-Ali et al. | |
| 8,346,330 B2 | 1/2013 | Lamego | |
| 8,353,842 B2 | 1/2013 | Al-Ali et al. | |
| 8,355,766 B2 | 1/2013 | MacNeish, III et al. | |
| 8,359,080 B2 | 1/2013 | Diab et al. | |
| 8,364,223 B2 | 1/2013 | Al-Ali et al. | |
| 8,364,226 B2 | 1/2013 | Diab et al. | |
| 8,374,665 B2 | 2/2013 | Lamego | |
| 8,385,995 B2 | 2/2013 | Al-Ali et al. | |
| 8,385,996 B2 | 2/2013 | Smith et al. | |
| 8,388,353 B2 | 3/2013 | Kiani et al. | |
| 8,399,822 B2 | 3/2013 | Al-Ali | |
| 8,401,602 B2 | 3/2013 | Kiani | |
| 8,405,608 B2 | 3/2013 | Al-Ali et al. | |
| 8,414,499 B2 | 4/2013 | Al-Ali et al. | |
| 8,418,524 B2 | 4/2013 | Al-Ali | |

(56) References Cited

U.S. PATENT DOCUMENTS

| | | | |
|---|---|---|---|
| 8,423,106 B2 | 4/2013 | Lamego et al. |
| 8,428,967 B2 | 4/2013 | Olsen et al. |
| 8,430,817 B1 | 4/2013 | Al-Ali et al. |
| 8,437,825 B2 | 5/2013 | Dalvi et al. |
| 8,455,290 B2 | 6/2013 | Siskavich |
| 8,457,703 B2 | 6/2013 | Al-Ali |
| 8,457,707 B2 | 6/2013 | Kiani |
| 8,463,349 B2 | 6/2013 | Diab et al. |
| 8,466,286 B2 | 6/2013 | Bellott et al. |
| 8,471,713 B2 | 6/2013 | Poeze et al. |
| 8,473,020 B2 | 6/2013 | Kiani et al. |
| 8,483,787 B2 | 7/2013 | Al-Ali et al. |
| 8,489,364 B2 | 7/2013 | Weber et al. |
| 8,498,684 B2 | 7/2013 | Weber et al. |
| 8,504,128 B2 | 8/2013 | Blank et al. |
| 8,509,867 B2 | 8/2013 | Workman et al. |
| 8,515,509 B2 | 8/2013 | Bruinsma et al. |
| 8,523,781 B2 | 9/2013 | Al-Ali |
| 8,529,301 B2 | 9/2013 | Al-Ali et al. |
| 8,532,727 B2 | 9/2013 | Ali et al. |
| 8,532,728 B2 | 9/2013 | Diab et al. |
| D692,145 S | 10/2013 | Al-Ali et al. |
| 8,547,209 B2 | 10/2013 | Kiani et al. |
| 8,548,548 B2 | 10/2013 | Al-Ali |
| 8,548,549 B2 | 10/2013 | Schurman et al. |
| 8,548,550 B2 | 10/2013 | Al-Ali et al. |
| 8,560,032 B2 | 10/2013 | Al-Ali et al. |
| 8,560,034 B1 | 10/2013 | Diab et al. |
| 8,570,167 B2 | 10/2013 | Al-Ali |
| 8,570,503 B2 | 10/2013 | Vo et al. |
| 8,571,617 B2 | 10/2013 | Reichgott et al. |
| 8,571,618 B1 | 10/2013 | Lamego et al. |
| 8,571,619 B2 | 10/2013 | Al-Ali et al. |
| 8,577,431 B2 | 11/2013 | Lamego et al. |
| 8,581,732 B2 | 11/2013 | Al-Ali et al. |
| 8,584,345 B2 | 11/2013 | Al-Ali et al. |
| 8,588,880 B2 | 11/2013 | Abdul-Hafiz et al. |
| 8,600,467 B2 | 12/2013 | Al-Ali et al. |
| 8,606,342 B2 | 12/2013 | Diab |
| 8,626,255 B2 | 1/2014 | Al-Ali et al. |
| 8,630,691 B2 | 1/2014 | Lamego et al. |
| 8,634,821 B2 * | 1/2014 | Raleigh ............... H04W 28/18 455/419 |
| 8,634,889 B2 | 1/2014 | Al-Ali et al. |
| 8,641,631 B2 | 2/2014 | Sierra et al. |
| 8,652,060 B2 | 2/2014 | Al-Ali |
| 8,663,107 B2 | 3/2014 | Kiani |
| 8,666,468 B1 | 3/2014 | Al-Ali |
| 8,667,967 B2 | 3/2014 | Al-Ali et al. |
| 8,670,811 B2 | 3/2014 | O'Reilly |
| 8,670,814 B2 | 3/2014 | Diab et al. |
| 8,676,286 B2 | 3/2014 | Weber et al. |
| 8,682,407 B2 | 3/2014 | Al-Ali |
| RE44,823 E | 4/2014 | Parker |
| RE44,875 E | 4/2014 | Kiani et al. |
| 8,688,183 B2 | 4/2014 | Bruinsma et al. |
| 8,690,799 B2 | 4/2014 | Telfort et al. |
| 8,700,112 B2 | 4/2014 | Kiani |
| 8,702,627 B2 | 4/2014 | Telfort et al. |
| 8,706,179 B2 | 4/2014 | Parker |
| 8,712,494 B1 | 4/2014 | MacNeish, III et al. |
| 8,715,206 B2 | 5/2014 | Telfort et al. |
| 8,718,735 B2 | 5/2014 | Lamego et al. |
| 8,718,737 B2 | 5/2014 | Diab et al. |
| 8,718,738 B2 | 5/2014 | Blank et al. |
| 8,720,249 B2 | 5/2014 | Al-Ali |
| 8,721,541 B2 | 5/2014 | Al-Ali et al. |
| 8,721,542 B2 | 5/2014 | Al-Ali et al. |
| 8,723,677 B1 | 5/2014 | Kiani |
| 8,725,645 B1 * | 5/2014 | Montini ............... G06F 21/121 705/50 |
| 8,740,792 B1 | 6/2014 | Kiani et al. |
| 8,754,776 B2 | 6/2014 | Poeze et al. |
| 8,755,535 B2 | 6/2014 | Telfort et al. |
| 8,755,856 B2 | 6/2014 | Diab et al. |
| 8,755,872 B1 | 6/2014 | Marinow |
| 8,761,850 B2 | 6/2014 | Lamego |
| 8,764,671 B2 | 7/2014 | Kiani |
| 8,768,423 B2 | 7/2014 | Shakespeare et al. |
| 8,771,204 B2 | 7/2014 | Telfort et al. |
| 8,777,634 B2 | 7/2014 | Kiani et al. |
| 8,781,543 B2 | 7/2014 | Diab et al. |
| 8,781,544 B2 | 7/2014 | Al-Ali et al. |
| 8,781,549 B2 | 7/2014 | Al-Ali et al. |
| 8,788,003 B2 | 7/2014 | Schurman et al. |
| 8,790,268 B2 | 7/2014 | Al-Ali |
| 8,793,164 B2 | 7/2014 | Sendo et al. |
| 8,801,613 B2 | 8/2014 | Al-Ali et al. |
| 8,821,397 B2 | 9/2014 | Al-Ali et al. |
| 8,821,415 B2 | 9/2014 | Al-Ali et al. |
| 8,830,449 B1 | 9/2014 | Lamego et al. |
| 8,831,700 B2 | 9/2014 | Schurman et al. |
| 8,840,549 B2 | 9/2014 | Al-Ali et al. |
| 8,847,740 B2 | 9/2014 | Kiani et al. |
| 8,849,365 B2 | 9/2014 | Smith et al. |
| 8,852,094 B2 | 10/2014 | Al-Ali et al. |
| 8,852,994 B2 | 10/2014 | Wojtczuk et al. |
| 8,868,147 B2 | 10/2014 | Stippick et al. |
| 8,868,150 B2 | 10/2014 | Al-Ali et al. |
| 8,870,792 B2 | 10/2014 | Al-Ali et al. |
| 8,886,271 B2 | 11/2014 | Kiani et al. |
| 8,888,539 B2 | 11/2014 | Al-Ali et al. |
| 8,888,708 B2 | 11/2014 | Diab et al. |
| 8,892,180 B2 | 11/2014 | Weber et al. |
| 8,897,847 B2 | 11/2014 | Al-Ali |
| 8,909,310 B2 | 12/2014 | Lamego et al. |
| 8,911,377 B2 | 12/2014 | Al-Ali |
| 8,912,909 B2 | 12/2014 | Al-Ali et al. |
| 8,920,317 B2 | 12/2014 | Al-Ali et al. |
| 8,921,699 B2 | 12/2014 | Al-Ali et al. |
| 8,922,382 B2 | 12/2014 | Al-Ali et al. |
| 8,929,964 B2 | 1/2015 | Al-Ali et al. |
| 8,942,777 B2 | 1/2015 | Diab et al. |
| 8,948,834 B2 | 2/2015 | Diab et al. |
| 8,948,835 B2 | 2/2015 | Diab |
| 8,965,471 B2 | 2/2015 | Lamego |
| 8,983,564 B2 | 3/2015 | Al-Ali |
| 8,989,831 B2 | 3/2015 | Al-Ali et al. |
| 8,996,085 B2 | 3/2015 | Kiani et al. |
| 8,998,809 B2 | 4/2015 | Kiani |
| D729,939 S | 5/2015 | Moom et al. |
| 9,028,429 B2 | 5/2015 | Telfort et al. |
| 9,037,207 B2 | 5/2015 | Al-Ali et al. |
| 9,060,721 B2 | 6/2015 | Reichgott et al. |
| 9,066,666 B2 | 6/2015 | Kiani |
| 9,066,680 B1 | 6/2015 | Al-Ali et al. |
| 9,069,069 B2 * | 6/2015 | Freund ............... G01S 19/14 |
| 9,072,474 B2 | 7/2015 | Al-Ali et al. |
| 9,078,560 B2 | 7/2015 | Schurman et al. |
| 9,084,569 B2 | 7/2015 | Weber et al. |
| 9,095,316 B2 | 8/2015 | Welch et al. |
| 9,106,038 B2 | 8/2015 | Telfort et al. |
| 9,107,625 B2 | 8/2015 | Telfort et al. |
| 9,107,626 B2 | 8/2015 | Al-Ali et al. |
| 9,113,831 B2 | 8/2015 | Al-Ali |
| 9,113,832 B2 | 8/2015 | Al-Ali |
| 9,119,595 B2 | 9/2015 | Lamego |
| 9,131,881 B2 | 9/2015 | Diab et al. |
| 9,131,882 B2 | 9/2015 | Al-Ali et al. |
| 9,131,883 B2 | 9/2015 | Al-Ali |
| 9,131,917 B2 | 9/2015 | Telfort et al. |
| 9,138,180 B1 | 9/2015 | Coverston et al. |
| 9,138,182 B2 | 9/2015 | Al-Ali et al. |
| 9,138,192 B2 | 9/2015 | Weber et al. |
| 9,142,117 B2 | 9/2015 | Muhsin et al. |
| D741,497 S | 10/2015 | Aber et al. |
| 9,153,112 B1 | 10/2015 | Kiani et al. |
| 9,153,121 B2 | 10/2015 | Kiani et al. |
| 9,161,696 B2 | 10/2015 | Al-Ali et al. |
| 9,161,713 B2 | 10/2015 | Al-Ali et al. |
| 9,167,995 B2 | 10/2015 | Lamego et al. |
| 9,176,141 B2 | 11/2015 | Al-Ali et al. |
| 9,178,859 B1 * | 11/2015 | Ortiz ............... G06F 21/64 |
| 9,186,102 B2 | 11/2015 | Bruinsma et al. |

(56) References Cited

U.S. PATENT DOCUMENTS

| | | |
|---|---|---|
| 9,192,312 B2 | 11/2015 | Al-Ali |
| 9,192,329 B2 | 11/2015 | Al-Ali |
| 9,192,351 B1 | 11/2015 | Telfort et al. |
| 9,195,385 B2 | 11/2015 | Al-Ali et al. |
| D745,167 S | 12/2015 | Canas et al. |
| D745,497 S | 12/2015 | Lee et al. |
| 9,211,072 B2 | 12/2015 | Kiani |
| 9,211,095 B1 | 12/2015 | Al-Ali |
| 9,215,075 B1 | 12/2015 | Poltorak |
| 9,218,454 B2 | 12/2015 | Kiani et al. |
| 9,226,696 B2 | 1/2016 | Kiani |
| 9,241,662 B2 | 1/2016 | Al-Ali et al. |
| 9,245,668 B1 | 1/2016 | Vo et al. |
| 9,251,007 B1 * | 2/2016 | Topham ............... G06F 21/73 |
| 9,259,185 B2 | 2/2016 | Abdul-Hafiz et al. |
| 9,267,572 B2 | 2/2016 | Barker et al. |
| 9,277,880 B2 | 3/2016 | Poeze et al. |
| 9,289,167 B2 | 3/2016 | Diab et al. |
| 9,295,421 B2 | 3/2016 | Kiani et al. |
| 9,307,928 B1 | 4/2016 | Al-Ali et al. |
| 9,323,894 B2 | 4/2016 | Kiani |
| D755,392 S | 5/2016 | Hwang et al. |
| 9,326,712 B1 | 5/2016 | Kiani |
| 9,333,316 B2 | 5/2016 | Kiani |
| 9,339,220 B2 | 5/2016 | Lamego et al. |
| 9,341,565 B2 | 5/2016 | Lamego et al. |
| 9,351,673 B2 | 5/2016 | Diab et al. |
| 9,351,675 B2 | 5/2016 | Al-Ali et al. |
| 9,364,181 B2 | 6/2016 | Kiani et al. |
| 9,368,671 B2 | 6/2016 | Wojtczuk et al. |
| 9,370,325 B2 | 6/2016 | Al-Ali et al. |
| 9,370,326 B2 | 6/2016 | McHale et al. |
| 9,370,335 B2 | 6/2016 | Al-Ali et al. |
| 9,375,185 B2 | 6/2016 | Ali et al. |
| 9,386,953 B2 | 7/2016 | Al-Ali |
| 9,386,961 B2 | 7/2016 | Al-Ali et al. |
| 9,392,945 B2 | 7/2016 | Al-Ali et al. |
| 9,397,448 B2 | 7/2016 | Al-Ali et al. |
| 9,408,542 B1 | 8/2016 | Kinast et al. |
| 9,436,645 B2 | 9/2016 | Al-Ali et al. |
| 9,445,759 B1 | 9/2016 | Lamego et al. |
| 9,466,919 B2 | 10/2016 | Kiani et al. |
| 9,474,474 B2 | 10/2016 | Lamego et al. |
| 9,480,422 B2 | 11/2016 | Al-Ali |
| 9,480,435 B2 | 11/2016 | Olsen |
| 9,492,110 B2 | 11/2016 | Al-Ali et al. |
| 9,510,779 B2 | 12/2016 | Poeze et al. |
| 9,517,024 B2 | 12/2016 | Kiani et al. |
| 9,532,722 B2 | 1/2017 | Lamego et al. |
| 9,538,949 B2 | 1/2017 | Al-Ali et al. |
| 9,538,980 B2 | 1/2017 | Telfort et al. |
| 9,549,696 B2 | 1/2017 | Lamego et al. |
| 9,554,737 B2 | 1/2017 | Schurman et al. |
| 9,560,996 B2 | 2/2017 | Kiani |
| 9,560,998 B2 | 2/2017 | Al-Ali et al. |
| 9,566,019 B2 | 2/2017 | Al-Ali et al. |
| 9,579,039 B2 | 2/2017 | Jansen et al. |
| 9,591,975 B2 | 3/2017 | Dalvi et al. |
| 9,622,692 B2 | 4/2017 | Lamego et al. |
| D788,312 S | 5/2017 | Al-Ali et al. |
| 9,649,054 B2 | 5/2017 | Lamego et al. |
| 9,697,928 B2 | 7/2017 | Al-Ali et al. |
| D794,803 S | 8/2017 | Thom |
| 9,717,458 B2 | 8/2017 | Lamego et al. |
| 9,724,016 B1 | 8/2017 | Al-Ali et al. |
| 9,724,024 B2 | 8/2017 | Al-Ali |
| 9,724,025 B1 | 8/2017 | Kiani et al. |
| 9,749,232 B2 | 8/2017 | Sampath et al. |
| 9,750,442 B2 | 9/2017 | Olsen |
| 9,750,461 B1 | 9/2017 | Telfort |
| 9,775,545 B2 | 10/2017 | Al-Ali et al. |
| 9,778,079 B1 | 10/2017 | Al-Ali et al. |
| 9,782,077 B2 | 10/2017 | Lamego et al. |
| 9,787,568 B2 | 10/2017 | Lamego et al. |
| 9,808,188 B1 | 11/2017 | Perea et al. |
| 9,839,379 B2 | 12/2017 | Al-Ali et al. |
| 9,839,381 B1 | 12/2017 | Weber et al. |
| 9,847,749 B2 | 12/2017 | Kiani et al. |
| 9,848,800 B1 | 12/2017 | Lee et al. |
| 9,861,298 B2 | 1/2018 | Eckerbom et al. |
| 9,861,305 B1 | 1/2018 | Weber et al. |
| 9,877,650 B2 | 1/2018 | Muhsin et al. |
| 9,891,079 B2 | 2/2018 | Dalvi |
| 9,924,897 B1 | 3/2018 | Abdul-Hafiz |
| 9,936,917 B2 | 4/2018 | Poeze et al. |
| 9,955,937 B2 | 5/2018 | Telfort |
| 9,965,946 B2 | 5/2018 | Al-Ali et al. |
| D820,865 S | 6/2018 | Muhsin et al. |
| 9,986,952 B2 | 6/2018 | Dalvi et al. |
| D822,215 S | 7/2018 | Al-Ali et al. |
| D822,216 S | 7/2018 | Barker et al. |
| 10,010,276 B2 | 7/2018 | Al-Ali et al. |
| 10,086,138 B1 | 10/2018 | Novak, Jr. |
| 10,111,591 B2 | 10/2018 | Dyell et al. |
| D833,624 S | 11/2018 | DeJong et al. |
| 10,123,729 B2 | 11/2018 | Dyell et al. |
| D835,282 S | 12/2018 | Barker et al. |
| D835,283 S | 12/2018 | Barker et al. |
| D835,284 S | 12/2018 | Barker et al. |
| D835,285 S | 12/2018 | Barker et al. |
| 10,149,616 B2 | 12/2018 | Al-Ali et al. |
| 10,154,815 B2 | 12/2018 | Al-Ali et al. |
| 10,159,412 B2 | 12/2018 | Lamego et al. |
| 10,188,348 B2 | 1/2019 | Al-Ali et al. |
| RE47,218 E | 2/2019 | Al-Ali |
| RE47,244 E | 2/2019 | Kiani et al. |
| RE47,249 E | 2/2019 | Kiani et al. |
| 10,205,291 B2 | 2/2019 | Scruggs et al. |
| 10,226,187 B2 | 3/2019 | Al-Ali et al. |
| 10,231,657 B2 | 3/2019 | Al-Ali et al. |
| 10,231,670 B2 | 3/2019 | Blank et al. |
| RE47,353 E | 4/2019 | Kiani et al. |
| 10,279,247 B2 | 5/2019 | Kiani |
| 10,292,664 B2 | 5/2019 | Al-Ali |
| 10,299,720 B2 | 5/2019 | Brown et al. |
| 10,305,775 B2 | 5/2019 | Lamego et al. |
| 10,327,337 B2 | 6/2019 | Schmidt et al. |
| 10,327,713 B2 | 6/2019 | Barker et al. |
| 10,332,630 B2 | 6/2019 | Al-Ali |
| 10,383,520 B2 | 8/2019 | Wojtczuk et al. |
| 10,383,527 B2 | 8/2019 | Al-Ali |
| 10,388,120 B2 | 8/2019 | Muhsin et al. |
| D864,120 S | 10/2019 | Forrest et al. |
| 10,441,181 B1 | 10/2019 | Telfort et al. |
| 10,441,196 B2 | 10/2019 | Eckerbom et al. |
| 10,448,844 B2 | 10/2019 | Al-Ali et al. |
| 10,448,871 B2 | 10/2019 | Al-Ali |
| 10,456,038 B2 | 10/2019 | Lamego et al. |
| 10,463,340 B2 | 11/2019 | Telfort et al. |
| 10,471,159 B1 | 11/2019 | Lapotko et al. |
| 10,505,311 B2 | 12/2019 | Al-Ali et al. |
| 10,524,738 B2 | 1/2020 | Olsen |
| 10,532,174 B2 | 1/2020 | Al-Ali |
| 10,537,285 B2 | 1/2020 | Shreim et al. |
| 10,542,903 B2 | 1/2020 | Al-Ali et al. |
| 10,555,678 B2 | 2/2020 | Dalvi et al. |
| 10,568,553 B2 | 2/2020 | O'Neil et al. |
| RE47,882 E | 3/2020 | Al-Ali |
| 10,608,817 B2 | 3/2020 | Haider et al. |
| D880,477 S | 4/2020 | Forrest et al. |
| 10,617,302 B2 | 4/2020 | Al-Ali et al. |
| 10,617,335 B2 | 4/2020 | Al-Ali et al. |
| 10,621,571 B2 * | 4/2020 | Martinez de Velasco Cortina ..... G06K 19/0723 |
| 10,637,181 B2 | 4/2020 | Al-Ali et al. |
| D887,548 S | 6/2020 | Abdul-Hafiz et al. |
| D887,549 S | 6/2020 | Abdul-Hafiz et al. |
| 10,667,764 B2 | 6/2020 | Ahmed et al. |
| D890,708 S | 7/2020 | Forrest et al. |
| 10,721,785 B2 | 7/2020 | Al-Ali |
| 10,736,518 B2 | 8/2020 | Al-Ali et al. |
| 10,750,984 B2 | 8/2020 | Pauley et al. |
| D897,098 S | 9/2020 | Al-Ali |
| 10,779,098 B2 | 9/2020 | Iswanto et al. |

(56) References Cited

U.S. PATENT DOCUMENTS

| | | |
|---|---|---|
| 10,827,961 B1 | 11/2020 | Iyengar et al. |
| 10,828,007 B1 | 11/2020 | Telfort et al. |
| 10,832,818 B2 | 11/2020 | Muhsin et al. |
| 10,849,554 B2 | 12/2020 | Shreim et al. |
| 10,856,750 B2 | 12/2020 | Indorf et al. |
| D906,970 S | 1/2021 | Forrest et al. |
| 10,918,281 B2 | 2/2021 | Al-Ali et al. |
| 10,932,705 B2 | 3/2021 | Muhsin et al. |
| 10,932,729 B2 | 3/2021 | Kiani et al. |
| 10,939,878 B2 | 3/2021 | Kiani et al. |
| D916,135 S | 4/2021 | Indorf et al. |
| D917,550 S | 4/2021 | Indorf et al. |
| D917,564 S | 4/2021 | Indorf et al. |
| D917,704 S | 4/2021 | Al-Ali et al. |
| 10,987,066 B2 | 4/2021 | Chandran et al. |
| 10,991,135 B2 | 4/2021 | Al-Ali et al. |
| D919,094 S | 5/2021 | Al-Ali et al. |
| D919,100 S | 5/2021 | Al-Ali et al. |
| 11,006,867 B2 | 5/2021 | Al-Ali |
| D921,202 S | 6/2021 | Al-All et al. |
| 11,024,064 B2 | 6/2021 | Muhsin et al. |
| 11,026,604 B2 | 6/2021 | Chen et al. |
| D925,597 S | 7/2021 | Chandran et al. |
| D927,699 S | 8/2021 | Al-Ali et al. |
| 11,076,777 B2 | 8/2021 | Lee et al. |
| 11,114,188 B2 | 9/2021 | Poeze et al. |
| 11,147,518 B1 | 10/2021 | Al-Ali et al. |
| 2001/0016877 A1* | 8/2001 | Dancs .................. G06Q 20/341 709/227 |
| 2001/0034477 A1 | 10/2001 | Mansfield et al. |
| 2001/0039483 A1 | 11/2001 | Brand et al. |
| 2002/0010401 A1 | 1/2002 | Bushmakin et al. |
| 2002/0013517 A1 | 1/2002 | West et al. |
| 2002/0013538 A1 | 1/2002 | Teller |
| 2002/0058864 A1 | 5/2002 | Mansfield et al. |
| 2002/0120467 A1 | 8/2002 | Buanes |
| 2002/0133080 A1 | 9/2002 | Apruzzese et al. |
| 2002/0138336 A1* | 9/2002 | Bakes .................. G06Q 10/087 705/28 |
| 2002/0147693 A1 | 10/2002 | Banerjee et al. |
| 2002/0152180 A1 | 10/2002 | Turgeon et al. |
| 2002/0178126 A1* | 11/2002 | Beck .................. H04L 67/34 705/75 |
| 2002/0184224 A1 | 12/2002 | Haff et al. |
| 2002/0198740 A1 | 12/2002 | Roman et al. |
| 2003/0013975 A1 | 1/2003 | Kiani |
| 2003/0018243 A1 | 1/2003 | Gerhardt et al. |
| 2003/0028495 A1 | 2/2003 | Pallante |
| 2003/0055794 A1* | 3/2003 | Johnson .......... G07B 17/00435 705/403 |
| 2003/0063913 A1* | 4/2003 | Yamazaki .......... G03G 15/502 399/8 |
| 2003/0093301 A1 | 5/2003 | Chesney et al. |
| 2003/0093668 A1* | 5/2003 | Multerer .................. A63F 13/71 713/161 |
| 2003/0115150 A1 | 6/2003 | Hamilton et al. |
| 2003/0144582 A1 | 7/2003 | Cohen et al. |
| 2003/0156288 A1 | 8/2003 | Barnum et al. |
| 2003/0212312 A1 | 11/2003 | Coffin, IV et al. |
| 2004/0030583 A1 | 2/2004 | Fleming |
| 2004/0068436 A1* | 4/2004 | Boubek .................. G06Q 30/02 705/14.71 |
| 2004/0068470 A1 | 4/2004 | Klyne |
| 2004/0071164 A1* | 4/2004 | Baum .................. H04L 45/00 370/469 |
| 2004/0106163 A1 | 6/2004 | Workman, Jr. et al. |
| 2004/0146328 A1* | 7/2004 | Sasayama .............. G03F 7/3071 400/118.2 |
| 2004/0162035 A1 | 8/2004 | Petersen et al. |
| 2004/0236699 A1* | 11/2004 | Beenau .................. G06Q 20/32 705/64 |
| 2004/0245330 A1* | 12/2004 | Swift .................. G06Q 40/02 235/379 |
| 2004/0267103 A1 | 12/2004 | Li et al. |
| 2004/0267552 A1* | 12/2004 | Gilliam .................. G06F 21/10 705/59 |
| 2005/0055276 A1 | 3/2005 | Kiani et al. |
| 2005/0108060 A1 | 5/2005 | Sasano |
| 2005/0125317 A1* | 6/2005 | Winkelman .......... G06Q 20/04 705/30 |
| 2005/0131810 A1 | 6/2005 | Garrett |
| 2005/0135306 A1 | 6/2005 | McAllen et al. |
| 2005/0165693 A1 | 7/2005 | Moritzen |
| 2005/0187787 A1 | 8/2005 | Tomlinson, Jr. et al. |
| 2005/0221276 A1 | 10/2005 | Rozakis et al. |
| 2005/0228242 A1 | 10/2005 | Kawamura et al. |
| 2005/0234317 A1 | 10/2005 | Kiani |
| 2005/0247778 A1* | 11/2005 | Roberts ............. G07G 1/0045 235/383 |
| 2006/0073719 A1 | 4/2006 | Kiani |
| 2006/0087407 A1 | 4/2006 | Stewart et al. |
| 2006/0149594 A1* | 7/2006 | Hilligoss .............. G06Q 50/22 705/2 |
| 2006/0167351 A1 | 7/2006 | Isaacson et al. |
| 2006/0189871 A1 | 8/2006 | Al-Ali et al. |
| 2006/0224059 A1 | 10/2006 | Swedlow et al. |
| 2006/0258917 A1* | 11/2006 | Burd .................. A61B 5/14532 600/309 |
| 2006/0259328 A1* | 11/2006 | Burd .................. A61B 5/14532 705/2 |
| 2007/0021843 A1* | 1/2007 | Neill .................. H04L 9/0897 700/1 |
| 2007/0022015 A1* | 1/2007 | Tarinelli ............. G06Q 30/06 705/5 |
| 2007/0027961 A1* | 2/2007 | Holzer .............. H04L 67/2814 709/219 |
| 2007/0043682 A1* | 2/2007 | Drapkin .............. G06Q 20/3829 705/71 |
| 2007/0073116 A1 | 3/2007 | Kiani et al. |
| 2007/0077912 A1* | 4/2007 | Mahajan .............. H04W 8/22 455/410 |
| 2007/0133767 A1* | 6/2007 | Hahn .................. H04M 15/00 379/114.2 |
| 2007/0180140 A1 | 8/2007 | Welch et al. |
| 2007/0181675 A1 | 8/2007 | Drummond et al. |
| 2007/0197881 A1 | 8/2007 | Wolf et al. |
| 2007/0198432 A1 | 8/2007 | Pitroda et al. |
| 2007/0213658 A1 | 9/2007 | Hickle |
| 2007/0226013 A1 | 9/2007 | Elletson et al. |
| 2007/0244377 A1 | 10/2007 | Cozad et al. |
| 2007/0293745 A1 | 12/2007 | McCutcheon et al. |
| 2007/0299318 A1 | 12/2007 | Chen et al. |
| 2008/0000479 A1 | 1/2008 | Elaz et al. |
| 2008/0015423 A1 | 1/2008 | Lam et al. |
| 2008/0046286 A1 | 2/2008 | Halsted |
| 2008/0064965 A1 | 3/2008 | Jay et al. |
| 2008/0089499 A1* | 4/2008 | Hahn .................. H04M 15/00 379/114.2 |
| 2008/0094228 A1 | 4/2008 | Welch et al. |
| 2008/0097908 A1* | 4/2008 | Dicks .................. G06F 19/3418 705/50 |
| 2008/0103375 A1 | 5/2008 | Kiani |
| 2008/0114695 A1* | 5/2008 | Gutierrez .......... G06Q 30/0601 705/59 |
| 2008/0179401 A1* | 7/2008 | Hart .................. G07F 7/0893 235/449 |
| 2008/0221418 A1 | 9/2008 | Al-Ali et al. |
| 2008/0242945 A1 | 10/2008 | Gugliotti et al. |
| 2008/0250029 A1* | 10/2008 | Fernandez .......... G06Q 30/0248 |
| 2008/0251579 A1* | 10/2008 | Larsen .................. G16H 10/60 235/380 |
| 2008/0281168 A1 | 11/2008 | Gibson et al. |
| 2008/0300572 A1 | 12/2008 | Rankers et al. |
| 2008/0319510 A1 | 12/2008 | Simpson et al. |
| 2009/0024528 A1 | 1/2009 | Otero |
| 2009/0036759 A1 | 2/2009 | Ault et al. |
| 2009/0047926 A1* | 2/2009 | Mastrantuono ....... H04M 17/20 455/405 |
| 2009/0076844 A1 | 3/2009 | Koegen |
| 2009/0081989 A1 | 3/2009 | Wuhrer |
| 2009/0093687 A1 | 4/2009 | Telfort et al. |
| 2009/0095926 A1 | 4/2009 | MacNeish, III |

(56) References Cited

U.S. PATENT DOCUMENTS

| | | | |
|---|---|---|---|
| 2009/0112769 A1* | 4/2009 | Dicks | H04L 9/3231 |
| | | | 705/51 |
| 2009/0119062 A1 | 5/2009 | Owens et al. | |
| 2009/0150170 A1* | 6/2009 | Junger | G06Q 30/018 |
| | | | 705/317 |
| 2009/0247984 A1 | 10/2009 | Lamego et al. | |
| 2009/0275813 A1 | 11/2009 | Davis | |
| 2009/0275844 A1 | 11/2009 | Al-Ali | |
| 2009/0293560 A1* | 12/2009 | Ikeguchi | G06F 21/88 |
| | | | 70/262 |
| 2009/0307142 A1 | 12/2009 | Mardikar | |
| 2010/0004518 A1 | 1/2010 | Vo et al. | |
| 2010/0030040 A1 | 2/2010 | Poeze et al. | |
| 2010/0056875 A1* | 3/2010 | Schoenberg | A61B 5/1112 |
| | | | 600/300 |
| 2010/0057556 A1* | 3/2010 | Rousso | G06Q 30/0245 |
| | | | 705/14.44 |
| 2010/0094951 A1* | 4/2010 | Furuta | G06F 11/00 |
| | | | 709/217 |
| 2010/0099964 A1 | 4/2010 | O'Reilly et al. | |
| 2010/0145833 A1 | 6/2010 | Hamilton, II et al. | |
| 2010/0169659 A1 | 7/2010 | Shnowske et al. | |
| 2010/0204557 A1* | 8/2010 | Kiaie | A61B 5/4839 |
| | | | 600/365 |
| 2010/0234718 A1 | 9/2010 | Sampath et al. | |
| 2010/0250400 A1* | 9/2010 | Fernandez | G06Q 30/0601 |
| | | | 705/26.1 |
| 2010/0254581 A1 | 10/2010 | Neeser et al. | |
| 2010/0268120 A1* | 10/2010 | Eriksen | A61B 5/6804 |
| | | | 600/587 |
| 2010/0270257 A1 | 10/2010 | Wachman et al. | |
| 2011/0004549 A1* | 1/2011 | Gray | G06F 21/572 |
| | | | 709/224 |
| 2011/0028806 A1 | 2/2011 | Merritt et al. | |
| 2011/0028809 A1 | 2/2011 | Goodman | |
| 2011/0040197 A1 | 2/2011 | Welch et al. | |
| 2011/0073644 A1* | 3/2011 | Sarkis, Jr | G07F 17/0014 |
| | | | 235/382 |
| 2011/0077484 A1 | 3/2011 | Van Slyke et al. | |
| 2011/0082711 A1 | 4/2011 | Poeze et al. | |
| 2011/0087081 A1 | 4/2011 | Kiani et al. | |
| 2011/0105854 A1 | 5/2011 | Kiani et al. | |
| 2011/0118561 A1 | 5/2011 | Tari et al. | |
| 2011/0119182 A1 | 5/2011 | Smolkin | |
| 2011/0137297 A1 | 6/2011 | Kiani et al. | |
| 2011/0172498 A1* | 7/2011 | Olsen | G06Q 40/00 |
| | | | 600/300 |
| 2011/0179405 A1* | 7/2011 | Dicks | G06F 8/61 |
| | | | 717/168 |
| 2011/0208015 A1 | 8/2011 | Welch et al. | |
| 2011/0208568 A1* | 8/2011 | Deitiker | G07B 15/063 |
| | | | 705/13 |
| 2011/0213212 A1 | 9/2011 | Al-Ali | |
| 2011/0230733 A1 | 9/2011 | Al-Ali | |
| 2011/0235792 A1* | 9/2011 | Foster | H04M 17/00 |
| | | | 379/114.2 |
| 2011/0237911 A1 | 9/2011 | Lamego et al. | |
| 2011/0238581 A1 | 9/2011 | Severson et al. | |
| 2011/0273294 A1* | 11/2011 | Harwell | G06Q 10/06 |
| | | | 340/572.1 |
| 2012/0059267 A1 | 3/2012 | Lamego et al. | |
| 2012/0109685 A1* | 5/2012 | Carter | G06Q 50/22 |
| | | | 705/3 |
| 2012/0123231 A1 | 5/2012 | O'Reilly | |
| 2012/0143754 A1* | 6/2012 | Patel | G06Q 20/4018 |
| | | | 705/41 |
| 2012/0143772 A1* | 6/2012 | Abadir | G06Q 20/401 |
| | | | 705/75 |
| 2012/0156337 A1* | 6/2012 | Studor | A47J 31/5251 |
| | | | 426/231 |
| 2012/0165629 A1 | 6/2012 | Merritt et al. | |
| 2012/0179006 A1 | 7/2012 | Jansen et al. | |
| 2012/0209082 A1 | 8/2012 | Al-Ali | |
| 2012/0209084 A1 | 8/2012 | Olsen et al. | |
| 2012/0226117 A1 | 9/2012 | Lamego et al. | |
| 2012/0239529 A1 | 9/2012 | Low et al. | |
| 2012/0283524 A1 | 11/2012 | Kiani et al. | |
| 2012/0296178 A1 | 11/2012 | Lamego et al. | |
| 2012/0319816 A1 | 12/2012 | Al-Ali | |
| 2012/0330112 A1 | 12/2012 | Lamego et al. | |
| 2013/0023775 A1 | 1/2013 | Lamego et al. | |
| 2013/0035167 A1* | 2/2013 | Angelakis | A63F 13/80 |
| | | | 463/42 |
| 2013/0041591 A1 | 2/2013 | Lamego | |
| 2013/0046204 A1 | 2/2013 | Lamego et al. | |
| 2013/0060147 A1 | 3/2013 | Welch et al. | |
| 2013/0066644 A1* | 3/2013 | Dicks | G06Q 50/22 |
| | | | 705/2 |
| 2013/0096405 A1 | 4/2013 | Garfio | |
| 2013/0096936 A1 | 4/2013 | Sampath et al. | |
| 2013/0097085 A1* | 4/2013 | Peckover | G06F 21/73 |
| | | | 705/50 |
| 2013/0103527 A1* | 4/2013 | Cho | G06Q 30/0601 |
| | | | 705/26.1 |
| 2013/0117155 A1* | 5/2013 | Glasgo | G06Q 30/00 |
| | | | 705/26.35 |
| 2013/0159456 A1* | 6/2013 | Daoud | G16H 10/60 |
| | | | 709/217 |
| 2013/0160082 A1* | 6/2013 | Miller | H04L 63/08 |
| | | | 726/3 |
| 2013/0190581 A1 | 7/2013 | Al-Ali et al. | |
| 2013/0211214 A1 | 8/2013 | Olsen | |
| 2013/0212381 A1* | 8/2013 | Bousamra | H04L 63/0823 |
| | | | 713/156 |
| 2013/0243021 A1 | 9/2013 | Siskavich | |
| 2013/0246132 A1* | 9/2013 | Buie | G06Q 20/20 |
| | | | 705/13 |
| 2013/0253334 A1 | 9/2013 | Al-Ali et al. | |
| 2013/0296672 A1 | 11/2013 | O'Neil et al. | |
| 2013/0312066 A1* | 11/2013 | Suarez | G16H 40/67 |
| | | | 726/4 |
| 2013/0317370 A1 | 11/2013 | Dalvi et al. | |
| 2013/0324808 A1 | 12/2013 | Al-Ali et al. | |
| 2013/0331670 A1 | 12/2013 | Kiani | |
| 2013/0338461 A1 | 12/2013 | Lamego et al. | |
| 2013/0345921 A1 | 12/2013 | Al-Ali et al. | |
| 2014/0012100 A1 | 1/2014 | Al-Ali et al. | |
| 2014/0012981 A1* | 1/2014 | Samuell | H04L 47/40 |
| | | | 709/224 |
| 2014/0034353 A1 | 2/2014 | Al-Ali et al. | |
| 2014/0037089 A1* | 2/2014 | Itoh | G09C 1/00 |
| | | | 380/46 |
| 2014/0038545 A1* | 2/2014 | Ramprasad | H04M 15/30 |
| | | | 455/405 |
| 2014/0051953 A1 | 2/2014 | Lamego et al. | |
| 2014/0066783 A1 | 3/2014 | Kiani et al. | |
| 2014/0077956 A1 | 3/2014 | Sampath et al. | |
| 2014/0081100 A1 | 3/2014 | Muhsin et al. | |
| 2014/0081175 A1 | 3/2014 | Telfort | |
| 2014/0094667 A1 | 4/2014 | Schurman et al. | |
| 2014/0099928 A1* | 4/2014 | Caldwell | H04W 48/02 |
| | | | 455/411 |
| 2014/0100434 A1 | 4/2014 | Diab et al. | |
| 2014/0106706 A1* | 4/2014 | Tan | G06Q 20/349 |
| | | | 455/408 |
| 2014/0114199 A1 | 4/2014 | Lamego et al. | |
| 2014/0120564 A1 | 5/2014 | Workman et al. | |
| 2014/0121482 A1 | 5/2014 | Merritt et al. | |
| 2014/0121483 A1 | 5/2014 | Kiani | |
| 2014/0127137 A1 | 5/2014 | Bellott et al. | |
| 2014/0129702 A1* | 5/2014 | Lamego | G06Q 20/145 |
| | | | 709/224 |
| 2014/0135588 A1 | 5/2014 | Al-Ali et al. | |
| 2014/0142401 A1 | 5/2014 | Al-Ali et al. | |
| 2014/0163344 A1 | 6/2014 | Al-Ali | |
| 2014/0163402 A1 | 6/2014 | Lamego et al. | |
| 2014/0165149 A1* | 6/2014 | Chen | H04L 63/10 |
| | | | 726/4 |
| 2014/0166076 A1 | 6/2014 | Kiani et al. | |
| 2014/0171763 A1 | 6/2014 | Diab | |

(56) References Cited

U.S. PATENT DOCUMENTS

| | | |
|---|---|---|
| 2014/0175165 A1* | 6/2014 | Havens .............. G06Q 30/0185 235/375 |
| 2014/0180038 A1 | 6/2014 | Kiani |
| 2014/0180154 A1 | 6/2014 | Sierra et al. |
| 2014/0180160 A1 | 6/2014 | Brown et al. |
| 2014/0181524 A1* | 6/2014 | Itoh ..................... G06F 21/30 713/174 |
| 2014/0187973 A1 | 7/2014 | Brown et al. |
| 2014/0194766 A1 | 7/2014 | Al-Ali et al. |
| 2014/0195044 A1* | 7/2014 | McQuade ................ B67D 7/00 700/237 |
| 2014/0206963 A1 | 7/2014 | Al-Ali |
| 2014/0213864 A1 | 7/2014 | Abdul-Hafiz et al. |
| 2014/0229331 A1* | 8/2014 | McIntosh ........... G06Q 30/0613 705/26.41 |
| 2014/0243627 A1 | 8/2014 | Diab et al. |
| 2014/0266790 A1 | 9/2014 | Al-Ali et al. |
| 2014/0275808 A1 | 9/2014 | Poeze et al. |
| 2014/0275835 A1 | 9/2014 | Lamego et al. |
| 2014/0275871 A1 | 9/2014 | Lamego et al. |
| 2014/0275872 A1 | 9/2014 | Merritt et al. |
| 2014/0275881 A1 | 9/2014 | Lamego et al. |
| 2014/0288400 A1 | 9/2014 | Diab et al. |
| 2014/0303520 A1 | 10/2014 | Telfort et al. |
| 2014/0316217 A1 | 10/2014 | Purdon et al. |
| 2014/0316218 A1 | 10/2014 | Purdon et al. |
| 2014/0316228 A1 | 10/2014 | Blank et al. |
| 2014/0323825 A1 | 10/2014 | Al-Ali et al. |
| 2014/0323897 A1 | 10/2014 | Brown et al. |
| 2014/0323898 A1 | 10/2014 | Purdon et al. |
| 2014/0330092 A1 | 11/2014 | Al-Ali et al. |
| 2014/0330098 A1 | 11/2014 | Merritt et al. |
| 2014/0330099 A1 | 11/2014 | Al-Ali et al. |
| 2014/0330993 A1* | 11/2014 | Raz ..................... G07G 3/003 710/36 |
| 2014/0336481 A1 | 11/2014 | Shakespeare et al. |
| 2014/0357966 A1 | 12/2014 | Al-Ali et al. |
| 2014/0358777 A1 | 12/2014 | Gueh |
| 2015/0005600 A1 | 1/2015 | Blank et al. |
| 2015/0011907 A1 | 1/2015 | Purdon et al. |
| 2015/0012231 A1 | 1/2015 | Poeze et al. |
| 2015/0018650 A1 | 1/2015 | Al-Ali et al. |
| 2015/0025406 A1 | 1/2015 | Al-Ali |
| 2015/0032029 A1 | 1/2015 | Al-Ali et al. |
| 2015/0032569 A1* | 1/2015 | Stromberg ......... G06Q 30/0609 705/26.35 |
| 2015/0038859 A1 | 2/2015 | Dalvi et al. |
| 2015/0045637 A1 | 2/2015 | Dalvi |
| 2015/0048159 A1* | 2/2015 | Martinez de Velasco Cortina ..... G06Q 20/342 235/379 |
| 2015/0051462 A1 | 2/2015 | Olsen |
| 2015/0073241 A1 | 3/2015 | Lamego |
| 2015/0073925 A1* | 3/2015 | Renfroe ................ G06Q 50/12 705/15 |
| 2015/0080754 A1 | 3/2015 | Purdon et al. |
| 2015/0087936 A1 | 3/2015 | Al-Ali et al. |
| 2015/0094546 A1 | 4/2015 | Al-Ali |
| 2015/0097701 A1 | 4/2015 | Muhsin et al. |
| 2015/0099950 A1 | 4/2015 | Al-Ali et al. |
| 2015/0099951 A1 | 4/2015 | Al-Ali et al. |
| 2015/0099955 A1 | 4/2015 | Al-Ali et al. |
| 2015/0101844 A1 | 4/2015 | Al-Ali et al. |
| 2015/0106121 A1 | 4/2015 | Muhsin et al. |
| 2015/0112151 A1 | 4/2015 | Muhsin et al. |
| 2015/0116076 A1 | 4/2015 | Al-Ali et al. |
| 2015/0126830 A1 | 5/2015 | Schurman et al. |
| 2015/0133755 A1 | 5/2015 | Smith et al. |
| 2015/0141781 A1 | 5/2015 | Weber et al. |
| 2015/0165312 A1 | 6/2015 | Kiani |
| 2015/0196237 A1 | 7/2015 | Lamego |
| 2015/0201874 A1 | 7/2015 | Diab |
| 2015/0207626 A1* | 7/2015 | Neftel ................. H04W 12/003 713/168 |
| 2015/0216459 A1 | 8/2015 | Al-Ali et al. |
| 2015/0230755 A1 | 8/2015 | Al-Ali et al. |
| 2015/0238722 A1 | 8/2015 | Al-Ali |
| 2015/0245773 A1 | 9/2015 | Lamego et al. |
| 2015/0245794 A1 | 9/2015 | Al-Ali |
| 2015/0257689 A1 | 9/2015 | Al-Ali et al. |
| 2015/0272514 A1 | 10/2015 | Kiani et al. |
| 2015/0351697 A1 | 12/2015 | Weber et al. |
| 2015/0351704 A1 | 12/2015 | Kiani et al. |
| 2015/0359429 A1 | 12/2015 | Al-Ali et al. |
| 2015/0366472 A1 | 12/2015 | Kiani |
| 2015/0366507 A1 | 12/2015 | Blank et al. |
| 2015/0374298 A1 | 12/2015 | Al-Ali et al. |
| 2015/0380875 A1 | 12/2015 | Coverston et al. |
| 2016/0000362 A1 | 1/2016 | Diab et al. |
| 2016/0005016 A1 | 1/2016 | Eliahu et al. |
| 2016/0007930 A1 | 1/2016 | Weber et al. |
| 2016/0029932 A1 | 2/2016 | Al-Ali |
| 2016/0045118 A1 | 2/2016 | Kiani |
| 2016/0051205 A1 | 2/2016 | Al-Ali et al. |
| 2016/0058338 A1 | 3/2016 | Schurman et al. |
| 2016/0058347 A1 | 3/2016 | Reichgott et al. |
| 2016/0066823 A1 | 3/2016 | Al-Ali et al. |
| 2016/0066824 A1 | 3/2016 | Al-Ali et al. |
| 2016/0066879 A1 | 3/2016 | Telfort et al. |
| 2016/0072429 A1 | 3/2016 | Kiani et al. |
| 2016/0081552 A1 | 3/2016 | Wojtczuk et al. |
| 2016/0095543 A1 | 4/2016 | Telfort et al. |
| 2016/0095548 A1 | 4/2016 | Al-Ali et al. |
| 2016/0103598 A1 | 4/2016 | Al-Ali et al. |
| 2016/0110724 A1* | 4/2016 | Seto ..................... G06F 16/22 705/318 |
| 2016/0113527 A1 | 4/2016 | Al-Ali |
| 2016/0143548 A1 | 5/2016 | Al-Ali |
| 2016/0166182 A1 | 6/2016 | Al-Ali et al. |
| 2016/0166183 A1 | 6/2016 | Poeze et al. |
| 2016/0166188 A1 | 6/2016 | Bruinsma et al. |
| 2016/0166210 A1 | 6/2016 | Al-Ali |
| 2016/0192869 A1 | 7/2016 | Kiani et al. |
| 2016/0196388 A1 | 7/2016 | Lamego |
| 2016/0197436 A1 | 7/2016 | Barker et al. |
| 2016/0213281 A1 | 7/2016 | Eckerbom et al. |
| 2016/0228043 A1 | 8/2016 | O'Neil et al. |
| 2016/0233632 A1 | 8/2016 | Scruggs et al. |
| 2016/0234944 A1 | 8/2016 | Schmidt et al. |
| 2016/0270735 A1 | 9/2016 | Diab et al. |
| 2016/0283665 A1 | 9/2016 | Sampath et al. |
| 2016/0287090 A1 | 10/2016 | Al-Ali et al. |
| 2016/0287786 A1 | 10/2016 | Kiani |
| 2016/0296169 A1 | 10/2016 | McHale et al. |
| 2016/0310052 A1 | 10/2016 | Al-Ali et al. |
| 2016/0314260 A1 | 10/2016 | Kiani |
| 2016/0324486 A1 | 11/2016 | Al-Ali et al. |
| 2016/0324488 A1 | 11/2016 | Olsen |
| 2016/0327984 A1 | 11/2016 | Al-Ali et al. |
| 2016/0328528 A1 | 11/2016 | Al-Ali et al. |
| 2016/0331332 A1 | 11/2016 | Al-Ali |
| 2016/0367173 A1 | 12/2016 | Dalvi et al. |
| 2017/0007134 A1 | 1/2017 | Al-Ali et al. |
| 2017/0007190 A1 | 1/2017 | Al-Ali et al. |
| 2017/0007198 A1 | 1/2017 | Al-Ali et al. |
| 2017/0014084 A1 | 1/2017 | Al-Ali et al. |
| 2017/0021099 A1 | 1/2017 | Al-Ali et al. |
| 2017/0024748 A1 | 1/2017 | Haider |
| 2017/0027456 A1 | 2/2017 | Kinast et al. |
| 2017/0042488 A1 | 2/2017 | Muhsin |
| 2017/0055847 A1 | 3/2017 | Kiani et al. |
| 2017/0055851 A1 | 3/2017 | Al-Ali |
| 2017/0055882 A1 | 3/2017 | Al-Ali et al. |
| 2017/0055887 A1 | 3/2017 | Al-Ali |
| 2017/0055896 A1 | 3/2017 | Al-Ali |
| 2017/0079594 A1 | 3/2017 | Telfort et al. |
| 2017/0086723 A1 | 3/2017 | Al-Ali et al. |
| 2017/0173632 A1 | 6/2017 | Al-Ali |
| 2017/0251974 A1 | 9/2017 | Shreim et al. |
| 2017/0311891 A1 | 11/2017 | Kiani et al. |
| 2018/0103874 A1 | 4/2018 | Lee et al. |
| 2018/0199871 A1 | 7/2018 | Pauley et al. |
| 2018/0213583 A1 | 7/2018 | Al-Ali |

(56) References Cited

U.S. PATENT DOCUMENTS

| | | |
|---|---|---|
| 2018/0242926 A1 | 8/2018 | Muhsin et al. |
| 2018/0247353 A1 | 8/2018 | Al-Ali et al. |
| 2018/0247712 A1 | 8/2018 | Muhsin et al. |
| 2018/0256087 A1 | 9/2018 | Al-Ali et al. |
| 2018/0296161 A1 | 10/2018 | Shreim et al. |
| 2018/0300919 A1 | 10/2018 | Muhsin et al. |
| 2018/0310822 A1 | 11/2018 | Indorf et al. |
| 2018/0310823 A1 | 11/2018 | Al-Ali et al. |
| 2018/0317826 A1 | 11/2018 | Muhsin et al. |
| 2019/0015023 A1 | 1/2019 | Monfre |
| 2019/0034775 A1* | 1/2019 | Martinez de Velasco Cortina ..... G06Q 50/30 |
| 2019/0117070 A1 | 4/2019 | Muhsin et al. |
| 2019/0200941 A1 | 7/2019 | Chandran et al. |
| 2019/0239787 A1 | 8/2019 | Pauley et al. |
| 2019/0320906 A1 | 10/2019 | Olsen |
| 2019/0374139 A1 | 12/2019 | Kiani et al. |
| 2019/0374173 A1 | 12/2019 | Kiani et al. |
| 2019/0374713 A1 | 12/2019 | Kiani et al. |
| 2019/0386908 A1 | 12/2019 | Lamego et al. |
| 2020/0021930 A1 | 1/2020 | Iswanto et al. |
| 2020/0060869 A1 | 2/2020 | Telfort et al. |
| 2020/0111552 A1 | 4/2020 | Ahmed |
| 2020/0113435 A1 | 4/2020 | Muhsin |
| 2020/0113488 A1 | 4/2020 | Al-Ali et al. |
| 2020/0113496 A1 | 4/2020 | Scruggs et al. |
| 2020/0113497 A1 | 4/2020 | Triman et al. |
| 2020/0113520 A1 | 4/2020 | Abdul-Hafiz et al. |
| 2020/0138288 A1 | 5/2020 | Al-Ali et al. |
| 2020/0138368 A1 | 5/2020 | Kiani et al. |
| 2020/0163597 A1 | 5/2020 | Dalvi et al. |
| 2020/0196877 A1 | 6/2020 | Vo et al. |
| 2020/0253474 A1 | 8/2020 | Muhsin et al. |
| 2020/0253544 A1 | 8/2020 | Belur Nagaraj et al. |
| 2020/0275841 A1 | 9/2020 | Telfort et al. |
| 2020/0288983 A1 | 9/2020 | Telfort et al. |
| 2020/0321793 A1 | 10/2020 | Al-Ali et al. |
| 2020/0329983 A1 | 10/2020 | Al-Ali et al. |
| 2020/0329984 A1 | 10/2020 | Al-Ali et al. |
| 2020/0329993 A1 | 10/2020 | Al-Ali et al. |
| 2020/0330037 A1 | 10/2020 | Al-Ali et al. |
| 2021/0022628 A1 | 1/2021 | Telfort et al. |
| 2021/0104173 A1 | 4/2021 | Pauley et al. |
| 2021/0113121 A1 | 4/2021 | Diab et al. |
| 2021/0117525 A1 | 4/2021 | Kiani et al. |
| 2021/0118581 A1 | 4/2021 | Kiani et al. |
| 2021/0121582 A1 | 4/2021 | Krishnamani et al. |
| 2021/0161465 A1 | 6/2021 | Barker et al. |
| 2021/0236729 A1 | 8/2021 | Kiani et al. |
| 2021/0256267 A1 | 8/2021 | Ranasinghe et al. |
| 2021/0256835 A1 | 8/2021 | Ranasinghe et al. |
| 2021/0275101 A1 | 9/2021 | Vo et al. |
| 2021/0290060 A1 | 9/2021 | Ahmed |
| 2021/0290072 A1 | 9/2021 | Forrest |
| 2021/0290080 A1 | 9/2021 | Ahmed |
| 2021/0290120 A1 | 9/2021 | Al-Ali |
| 2021/0290177 A1 | 9/2021 | Novak, Jr. |
| 2021/0290184 A1 | 9/2021 | Ahmed |
| 2021/0296008 A1 | 9/2021 | Novak, Jr. |
| 2021/0330228 A1 | 10/2021 | Olsen et al. |

FOREIGN PATENT DOCUMENTS

| | | |
|---|---|---|
| JP | H10-314149 | 12/1998 |
| JP | 2002-268764 | 9/2002 |
| JP | 2002-351564 | 12/2002 |
| JP | 2003-502092 | 1/2003 |
| JP | 2003-521985 | 7/2003 |
| JP | 2003-296114 | 10/2003 |
| JP | 2004-164597 | 6/2004 |
| JP | 2009-528909 | 8/2009 |
| WO | WO 01/017450 | 3/2001 |
| WO | WO 02/017779 | 3/2002 |
| WO | WO 2006/051461 | 5/2006 |
| WO | WO 2007/108513 | 9/2007 |
| WO | WO 2007/143626 | 12/2007 |
| WO | WO 2011/032177 | 3/2011 |
| WO | WO 2018/201078 | 4/2018 |

OTHER PUBLICATIONS

US 9,579,050 B2, 02/2017, Al-Ali (withdrawn)

"E-ZPass Quick Guide" https://web.archive.org/web/20121217041418/https://www.e-zpassny.com/en/about/i_guide.pdf as archived on Jan. 6, 2012.

E-ZPass User's Manual https://web.archive.org/web/20120417132149/http://www.paturnpike.com/ezpass/pdf/EZPass_User_Manual.pdf as archived on Apr. 17, 2012.

Office Action in European Application No. 13191585.2, dated Nov. 14, 2014.

* cited by examiner

PHYSIOLOGICAL TEST CREDIT METHOD

PRIORITY CLAIM AND REFERENCE TO RELATED APPLICATIONS

The present application is a continuation of U.S. patent application Ser. No. 16/383,380, filed Apr. 12, 2019, titled Physiological Test Credit Method, which is a continuation of U.S. patent application Ser. No. 15/713,275, filed Sep. 22, 2017, titled Physiological Test Credit Method, which is a continuation of U.S. patent application Ser. No. 14/071,447, filed Nov. 4, 2013, now U.S. Pat. No. 9,787,568, titled Physiological Test Credit Method, which claims priority benefit under 35 U.S.C. § 119(e) to U.S. Provisional Patent Application Ser. No. 61/722,245, filed Nov. 5, 2012, titled Physiological Test Credit System, the entirety of each of which is hereby incorporated by reference herein.

BACKGROUND OF THE INVENTION

Pulse oximetry is a widely accepted noninvasive procedure for measuring the oxygen saturation level of arterial blood, an indicator of a person's oxygen supply. A typical pulse oximetry system utilizes a sensor applied to a patient tissue site. The sensor has emitters that transmit optical radiation having red and infrared (IR) wavelengths into the tissue site. A detector responds to the intensity of the optical radiation after attenuation by pulsatile arterial blood flowing within the tissue site. Based on this response, a processor determines measurements for oxygen saturation and pulse rate. In addition, a pulse oximeter may display a plethysmograph waveform, which is a visualization of blood volume change within the illuminated tissue caused by the pulsatile arterial blood flow over time.

Pulse oximeters capable of reading through motion induced noise are available from Masimo Corporation ("Masimo") Irvine, Calif. Moreover, portable and other pulse oximeters capable of reading through motion induced noise are disclosed in at least U.S. Pat. Nos. 6,770,028, 6,658,276, 6,157,850, 6,002,952 5,769,785, and 5,758,644, which are all assigned to Masimo and are all incorporated in their entireties by reference herein. Corresponding low noise sensors are also available from Masimo and are disclosed in at least U.S. Pat. Nos. 6,985,764, 6,813,511, 6,792,300, 6,256,523, 6,088,607, 5,782,757 and 5,638,818, which are all assigned to Masimo and are all incorporated in their entireties by reference herein. Such reading through motion pulse oximeters and low noise sensors have gained rapid acceptance in a wide variety of medical applications, including surgical wards, intensive care and neonatal units, general wards, home care, physical training, and virtually all types of monitoring scenarios.

Noninvasive blood parameter monitors capable of measuring blood parameters in addition to $SpO_2$, such as HbCO, HbMet and total hemoglobin (Hbt) and corresponding multiple wavelength optical sensors are also available from Masimo. Noninvasive blood parameter monitors and corresponding multiple wavelength optical sensors are described in at least U.S. patent application Ser. No. 11/367,013, filed Mar. 1, 2006 and entitled Multiple Wavelength Sensor Emitters and U.S. patent application Ser. No. 11/366,208, filed Mar. 1, 2006 and entitled Noninvasive Multi-Parameter Patient Monitor, both assigned to Cercacor Laboratories, Inc. ("Cercacor") Irvine, Calif. and both incorporated in their entireties by reference herein.

Further, physiological monitoring systems that include low noise optical sensors and pulse oximetry monitors, such as any of LNOP® adhesive or reusable sensors, SofTouch™ sensors, Hi-Fi Trauma™ or Blue™ sensors; and any of Radical®, SatShare™, Rad-9™, Rad-5™, Rad-5v™ or PPO+™ Masimo SET® pulse oximeters, are all available from Masimo. Physiological monitoring systems including multiple wavelength sensors and corresponding noninvasive blood parameter monitors, such as Rainbow™ adhesive and reusable sensors and RAD-57™ and Radical-7™ monitors for measuring $SpO_2$, pulse rate, perfusion index, signal quality, HbCO and HbMet among other parameters are also available from Masimo.

SUMMARY OF THE INVENTION

A physiological monitoring system has a sensor that transmits optical radiation at a multiplicity of wavelengths and a monitor that determines the relative concentrations of blood constituents such as $HbO_2$, Hb, carboxyhemoglobin (HbCO), methemoglobin (MetHb), fractional oxygen saturation, total hemoglobin (Hbt) and blood glucose to name a few. The monitor advantageously utilizes test credits each of which represent a quantum of currency. A test credit enables the monitor to make a physiological measurement. In various embodiments different monitor buttons are pressed to measure different variables. For example, one button initiates a $SpO_2$ measurement and another button initiates a SpCO measurement. After the measurement, the number of available test credits are decremented. The sensor has a memory that stores the test credits, which is decremented after each test. The monitor reads the sensor memory so as to determine the remaining test credits. Physiological monitoring systems include a Masimo Pronto-7® and corresponding rainbow 4D™ DC sensor. The Pronto-7 is a palm-sized device designed for quick-and-easy noninvasive total hemoglobin (SpHb®) spot-check testing, along with $SpO_2$, pulse rate, and perfusion index. A spot check monitor and corresponding credit system is described in U.S. patent application Ser. No. 12/882,111 titled Spot Check Monitor Credit System, filed Sep. 14, 2010 and U.S. patent application Ser. No. 13/110,833 titled Spot Check Monitor Credit System, filed May 18, 2011, both assigned to Cercacor and both incorporated in their entireties by reference herein.

An aspect of a physiological test credit method programmatically initiates wireless communications between a physiological monitor and a remote server in response to available test credits falling below a predetermined threshold so as to download additional test credits from the server to the monitor and therefore enable the monitor to perform additional physiological parameter spot-checks on a per test credit basis. The physiological test credit system establishes a threshold for test credits stored in an optical sensor attached to a corresponding physiological monitor. A server is securely connected to the monitor when remaining test credits fall below the threshold, and test credits are downloaded from the server to the monitor accordingly. In various embodiments, a quantum of test credits is defined and an amount of test credits equal to the quantum is downloaded each time the remaining test credits fall below the threshold. A download frequency is defined according to the number of times remaining test credits fall below the threshold in a given period of time. The threshold is adjusted according to the download frequency. Alternatively, or in addition to adjusting the threshold, the quantum is adjusted according to the download frequency.

In various other embodiments, challenges are exchanged between the server and the monitor so as to verify both the server and the monitor. The challenges may include sending a server challenge code to the monitor and breaking the server challenge code with the monitor and sending a monitor challenge code to the server and breaking the monitor challenge code with the server. The monitor may be validated utilizing sales data. Also, the server may send a request for device serial numbers to the monitor, and the serial numbers are matched to sales data. Further, monitor validation may include sending a server request for a zip code to the monitor and matching the zip code to the monitor account.

Another aspect a physiological test credit method is determining a test credit quantity associated with a physiological sensor, comparing the test credit quantity to a threshold and wirelessly connecting a physiological monitor to a server if the test credit quantity is below the threshold. Server commands are processed so as to download additional test credits to the monitor. Additional test credits are transferred to the physiological sensor, and the physiological monitor is disconnected from the server.

In various embodiments, the frequency of test credit downloads are tracked and, at least periodically, the amount of additional test credits downloaded are adjusted according to the frequency. The threshold may be adjusted, at least periodically, according to the frequency. The monitor may be challenged to break a server code before any test credits are downloaded to the monitor. The server may be challenged to break a monitor code before any test credits are downloaded to the monitor.

A further aspect of a physiological test credit method comprises establishing a wireless connection between a monitor and a server; downloading a file of test credits from the server to the monitor; transferring the test credits to a sensor in communications with the monitor; performing a physiological test on a person using the sensor; displaying a result of the physiological test on the monitor; deducting a test credit from the sensor in response to the test; and downloading an additional file of test credits from the server to the monitor in response to the number of test credits remaining in the sensor falling below a threshold.

In various embodiments, a quantity of test credits contained in the additional file are defined and adjusted according to the time between the downloading of the file and the downloading of the additional file. The threshold is adjusted according to the time between the downloading of the file and the downloading of the additional file. A two-way challenge is performed between the monitor and the server before downloading a file of test credits. The two-way challenge comprises sending a server challenge code to the monitor; breaking the server challenge code at the monitor; sending a monitor challenge code to the server; and breaking the monitor challenge code at the server. The sensor and the monitor serial numbers are sent to the server, and the serial numbers are matched with sales data available to the server. Monitor configuration parameters are saved on the server.

Yet another aspect of a physiological test credit system establishes wireless communications between a physiological monitor and a remote server. The server downloads test credits from the server to a sensor attached to the monitor. Each test credit allows the monitor to perform a spot-check of a physiological parameter. The monitor initiates a test credit download when the number of available test credits for a sensor falls below a test credit threshold. The monitor establishes a wireless connection with a server. The monitor and server perform a two-way challenge so that each can verify a connection to an approved device. The server also authenticates the monitor's account on the server. If the challenges and authentication are successful, the server downloads a credit file of test credits to the monitor and its attached sensor. The monitor and server then disconnect.

An additional aspect of a physiological test credit method establishes wireless communications between a physiological monitor and a remote server so as to download test credits to the monitor and its attached optical sensor. This enables the monitor to perform physiological parameter spot-checks on a per test credit basis. The physiological test credit method establishes a minimum threshold for test credits stored in an optical sensor attached to a corresponding physiological monitor and connects a server to the monitor when remaining test credits fall below the minimum threshold. The server-monitor connection first requires the monitor and server to exchange mutual code-breaking challenges for server-monitor verification. The server is then allowed to authenticate the monitor user account and funds. The server further validates the monitor via sales data. Monitor settings are saved to the server, and server commands are sent to the monitor.

In various embodiments, a server command is sent to the monitor to download configuration parameters including the test credit minimum threshold. The first time a monitor is connected to a server, a one-time monitor setup is performed. In exchanging challenges a server challenge code is sent to the monitor. The monitor must break the server challenge code. Then the monitor sends a challenge code to the server, which the server must break. Monitor validation involves a server request for device serial numbers from the monitor, which are matched with sales data. The server also requests a monitor zip code, which is matched with the monitor account. In various other embodiments, user settings are saved in the monitor and downloaded to the server. The server sends monitor commands that comprise OP commands to perform a monitor functions, GUI commands to display results and hybrid command to initiate a user response.

A further aspect of a physiological test credit method comprises establishing a wireless connection between a monitor and a server, performing a two-way challenge between the monitor and the server, authenticating the monitor and validating the monitor. The method may further comprise transferring a credit file of test credits from the server to the monitor, performing a physiological test, deducting a test credit corresponding to the test from the monitor account, and disconnecting the monitor and the server. The server also performs a one-time monitor setup.

In various embodiments, the two-way challenge includes sending a first challenge code from the server to the monitor, breaking the first challenge code at the monitor, sending a second challenge code from the monitor to the server and breaking the second challenge code at the server. A monitor validation comprises sending sensor and monitor serial numbers to the server, matching the serial numbers with sales data available to the server, sending a zip code to the server and matching the zip code with account information available to the server. Authenticating may comprise verifying the monitor's user account and funds. Setting-up the monitor may comprise sending commands and queries to the monitor so as to receive configuration parameters.

Another aspect of a physiological test credit method determines if test credits are available to the monitor and checks if a Wi-Fi connection is available. If test credits are less than a test credit threshold, the monitor connects to a test credit server, processes server commands so as to download test credits and disconnects from the server. In various embodiments, the monitor is challenged to break a server code, the server is challenged to break a monitor code. The server validates monitor serial codes, and saves monitor configuration parameters.

DETAILED DESCRIPTION OF THE PREFERRED EMBODIMENTS

Figure 1:
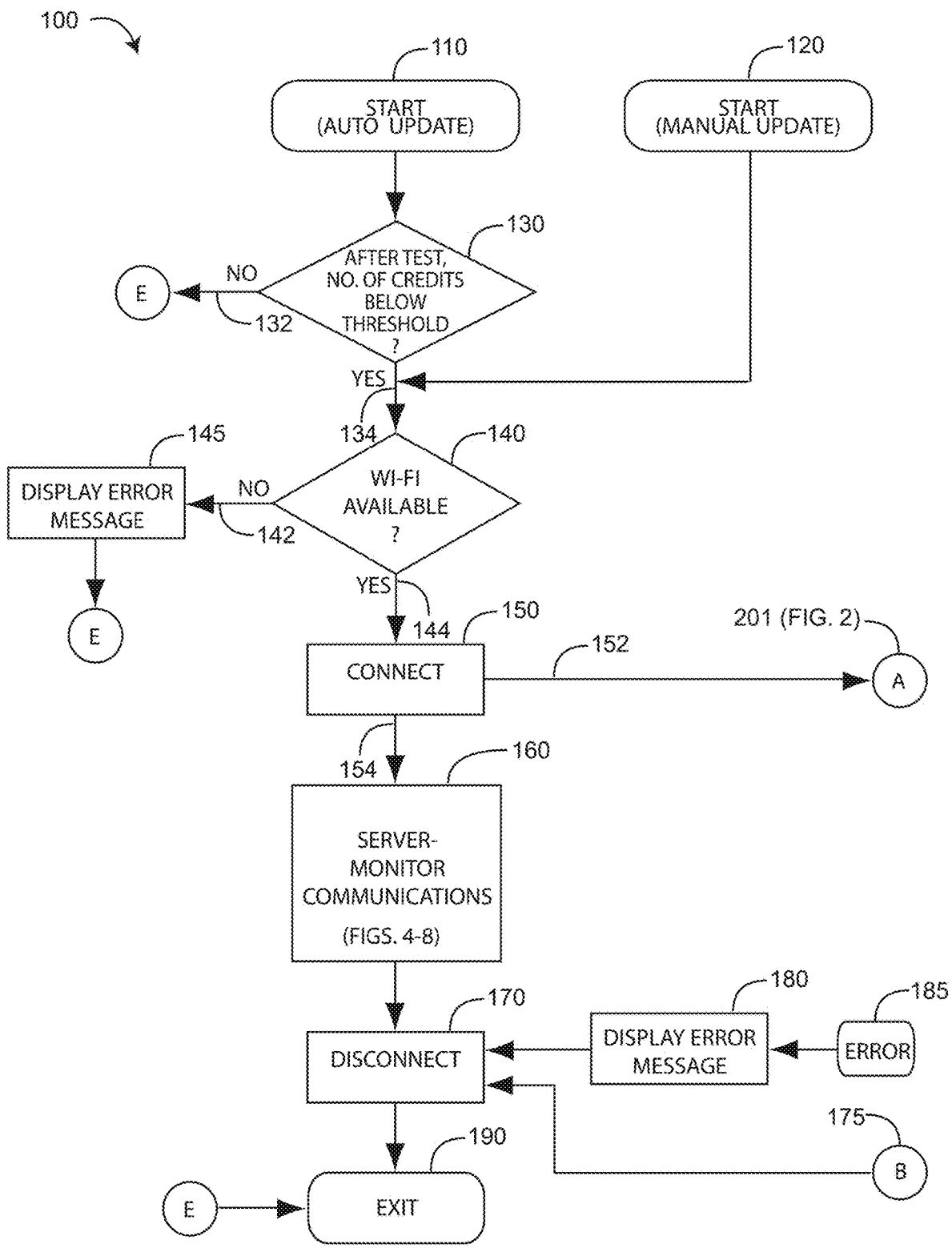
FIG. 1 is a flowchart of a monitor-side physiological test credit method.
Figure 2:
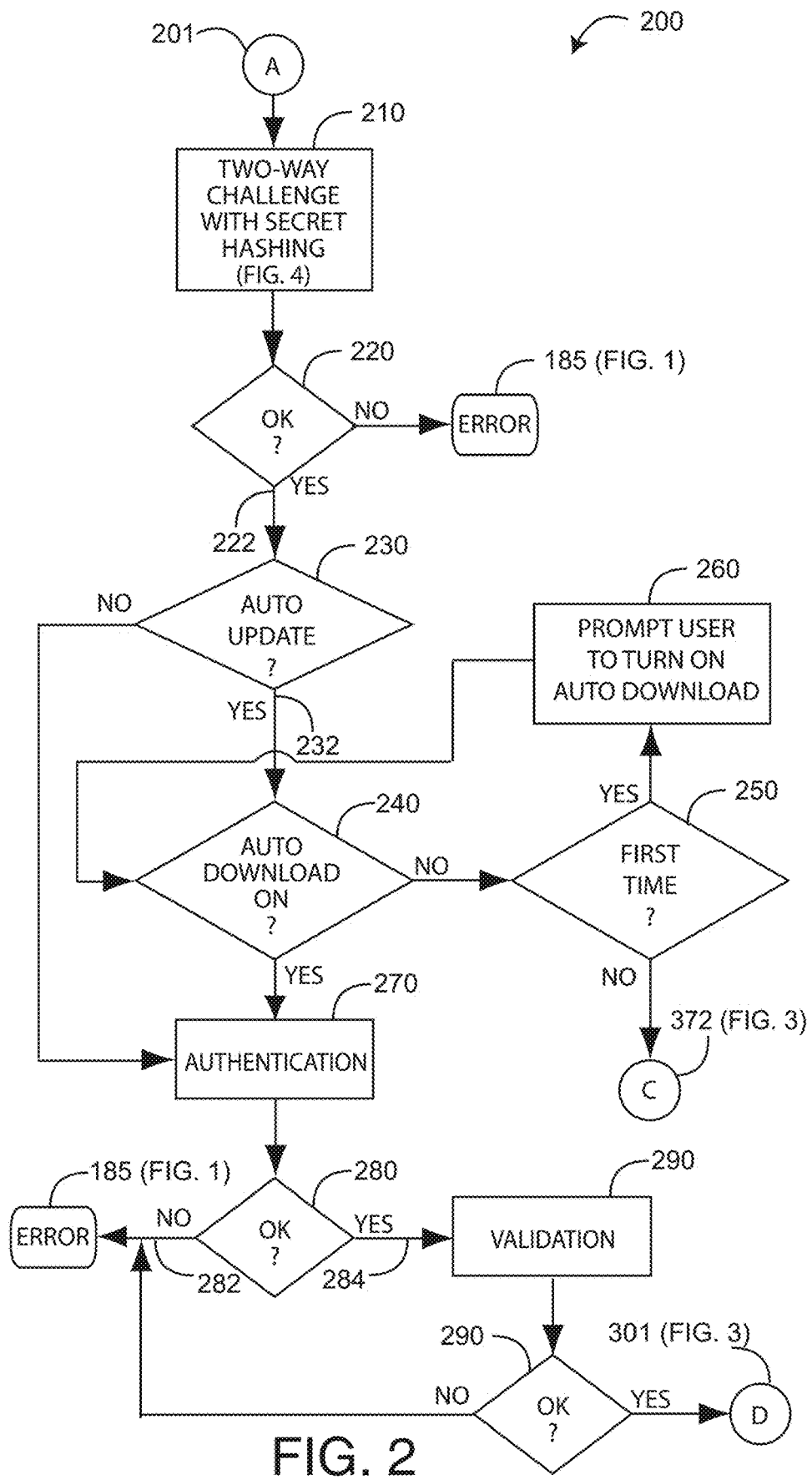
FIGS. 2-3 are flowcharts of a server-side physiological test credit method.
Figure 3:
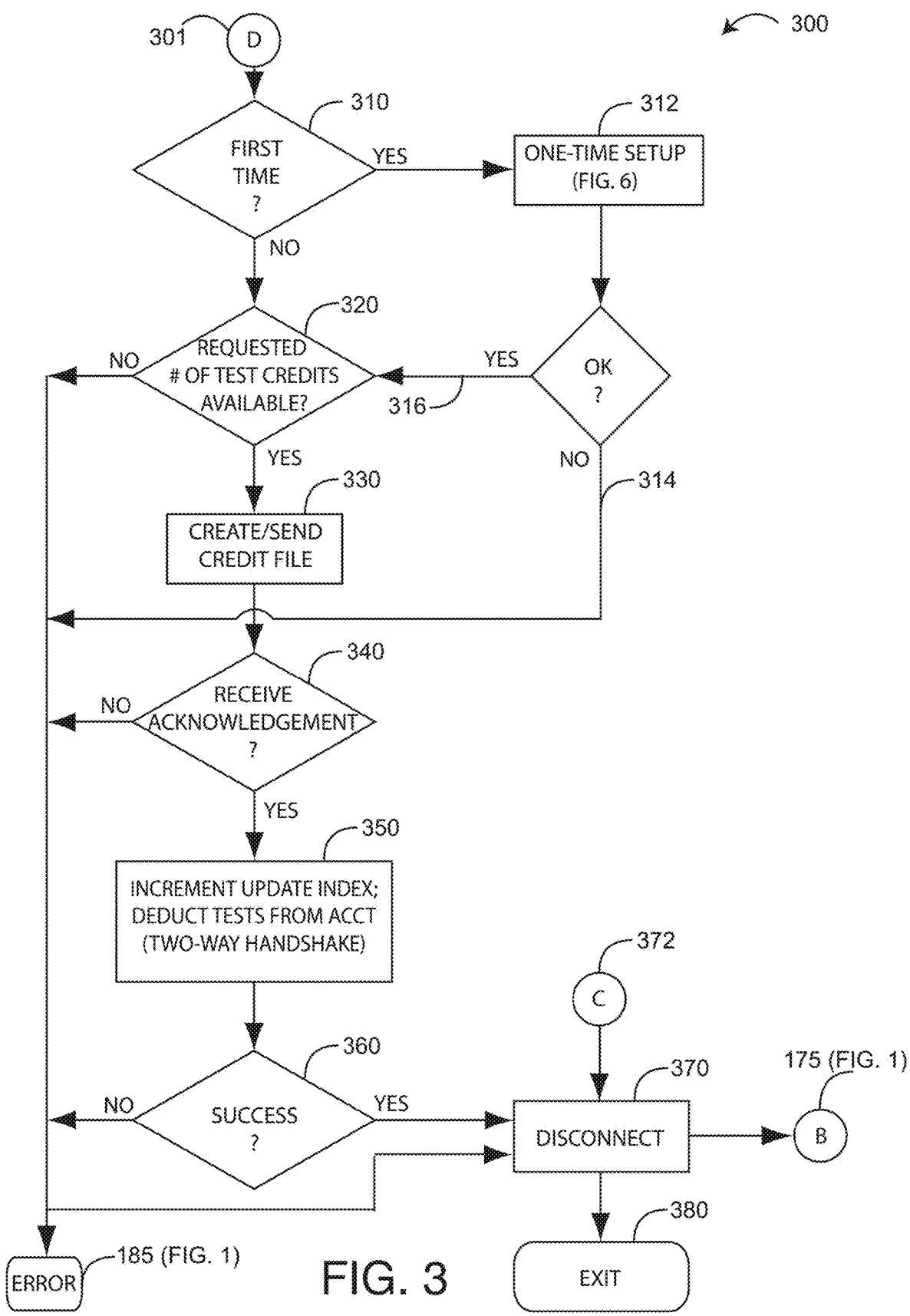

FIGS. 1-3 illustrate test credit downloads to a monitoring device using a broadband connection, such as Wi-Fi. In an embodiment, the monitor always initiates the connection. There are two ways a user can download test credits. "Automatic download" or "Manual download." For automatic downloads, the monitor initiates the connection after a test is performed and the available test credits fall below a predefined update threshold. For manual downloads, a user initiates the connection using a monitor menu flow. Accordingly, when a monitor initiates a connection, the initial connection request will have a parameter that describes whether or not a user manually initiated the connection.

For an automatic download, the monitor initiates a connection to a test credit server after a test is performed and the test credits drop below a user-predefined update threshold. In an embodiment, a user-predefined quantum of test credits (an integer between 1 and N inclusive) is downloaded each time the update threshold is crossed. In an embodiment, the test credit update threshold and the test credit download quantum are user-defined. In an embodiment, the monitor automatically adjusts the test credit download quantum and/or the test credit update threshold according to the frequency of test credit usage so as to advantageously reduce the frequency of server connections during periods of heavy monitor usage and to advantageously spread-out test credit expenditures during periods of light monitor usage. In an embodiment, the relationship between test credit download quantum, test credit update threshold and test credit usage is user defined.

The process of updating the test credits is done in the background. However, a user will not be able to perform a test during this period. If insufficient test credits are available for auto-download, a server may query/inform a user about this scenario via GUI commands to the monitor. A monitor initiates a manual download via a local GUI. Then the server takes over the process as with an auto download mode.

FIG. 1 illustrates a test credit download process from a monitor perspective 100. A monitor test credit download can be initiated automatically 110. After a test is complete, the number of available tests credits on a connected sensor is determined and compared with a specified update threshold 130. If the available test credits have not fallen below that threshold 132, the update process exits 190. If the number of test credits are below that threshold 134, the update process continues.

Also shown in FIG. 1, alternatively, a monitor test credit download can be initiated manually when a user selects a manual test credit update menu option 120. For either auto update 110 or manual update 120, Wi-Fi availability is determined 140. If there is no Wi-Fi 142, the process displays an error message 145 and exits 190. If Wi-Fi is available 144, a connection 150 to a server is attempted 152, as described below. Once a server connection is established 154, the monitor processes commands from the server 160, disconnects 170 and exits 190.

FIGS. 2-3 illustrate a test credit download process from a server perspective. As shown in FIG. 2, immediately after a Wi-Fi connection is established between monitor and server, the server initiates a two-way challenge with secret hashing 210. Both the server and the monitor use a two-way challenge to verify their connection with a real monitor or server, respectively, as described in detail with respect to FIG. 4, below. If the challenge 210 is successful 222, the server determines if the update is manual or automatic 230. If automatic 232, the server verifies that the user has turned on the auto download feature 240, prompting the user 250, 260 if necessary. If the auto download remains off, the server disconnects 372 (FIG. 3). With either the manual or automatic update, a secure authentication 270 is performed, which verifies the user's account and funds. If authentication fails 282, an error 185 (FIG. 1) is returned to the monitor, an error message is displayed 180 (FIG. 1) and the monitor disconnects 170 (FIG. 1). If authentication succeeds 284, validation is performed 301 (FIG. 3).

As shown in FIG. 2, once the user's account is authenticated, the customer and/or monitor and sensor are validated 290. In part, this step insures that customers, monitors and sensors are paired to the appropriate manufacturer or distributor. This can be a one-time validation or a validation for every credit download.

As shown in FIG. 3, when the server recognizes that a monitor is connecting for the first time 310, the server performs a one-time setup 312, as described with respect to FIG. 6, below. If there is any problems with the setup 314, the server sends an error 185 (FIG. 1) to the monitor, drops the connection 370 and exits 380. If the setup 312 is currently successful 316 or was previously performed 310, the server determines if the requested number of test credits are available 320. If so, the credit file is created and sent to the monitor 330. If not, an error is returned to the monitor 185 (FIG. 1), and the server disconnects 370 and exits 380.

Further shown in FIG. 3, after the monitor receives a credit file from the server 330. The monitor sends an ACK and the server receives the ACK 340. Using hand-shaking, either zero or all three of the following operations take place: the server deducts the credit from user account; the server increments the index count; and/or the monitor updates credits into the sensor 350.

Additionally shown in FIG. 3, the server drops the connection 370 upon successful completion of the process 360 or if it recognizes any error 185 (FIG. 1). The monitor drops the connection 170 (FIG. 1) if the server does not meet the monitor's challenge or the monitor recognizes an error 185 due to any reason.

Figure 4:
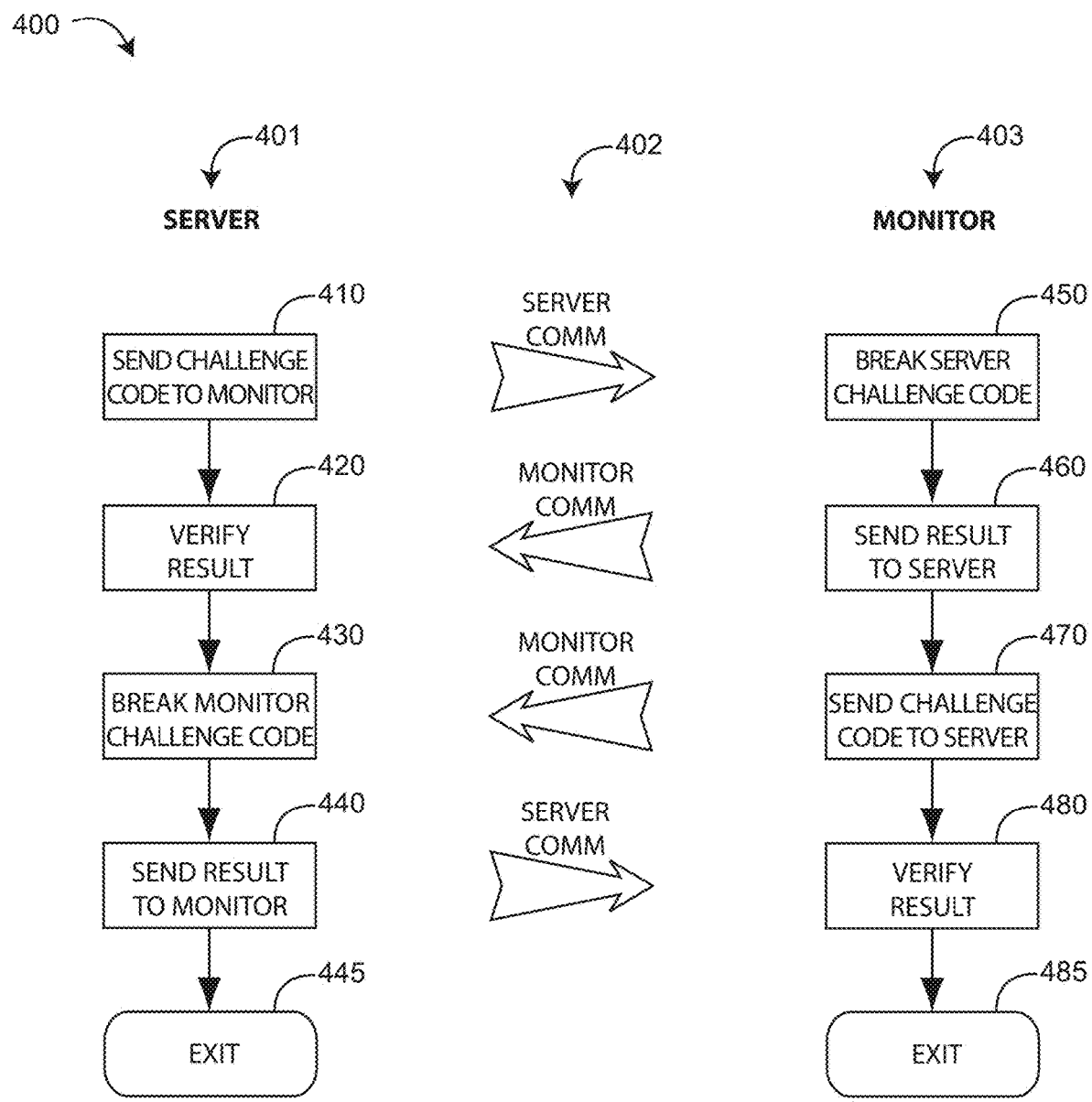
FIG. 4 is a flowchart of a two-way challenge for both the server and the monitor to verify their connections.

FIG. 4 illustrates the two-way challenge 400 for both the server 401 and the monitor 403 to verify their connections. In order to do that, both the monitor and the server challenge each other with a code to break, which only a real server and a real monitor know how to do. In particular, the server 410 first challenges the monitor 450 to break a code. If the server sees that the device cannot break the code 420, the server drops the connection. Otherwise, the server 430 asks the monitor 470 to send the server a code to break. If the monitor sees that the server cannot break the code 480, the monitor drops the connection.

Figure 5:
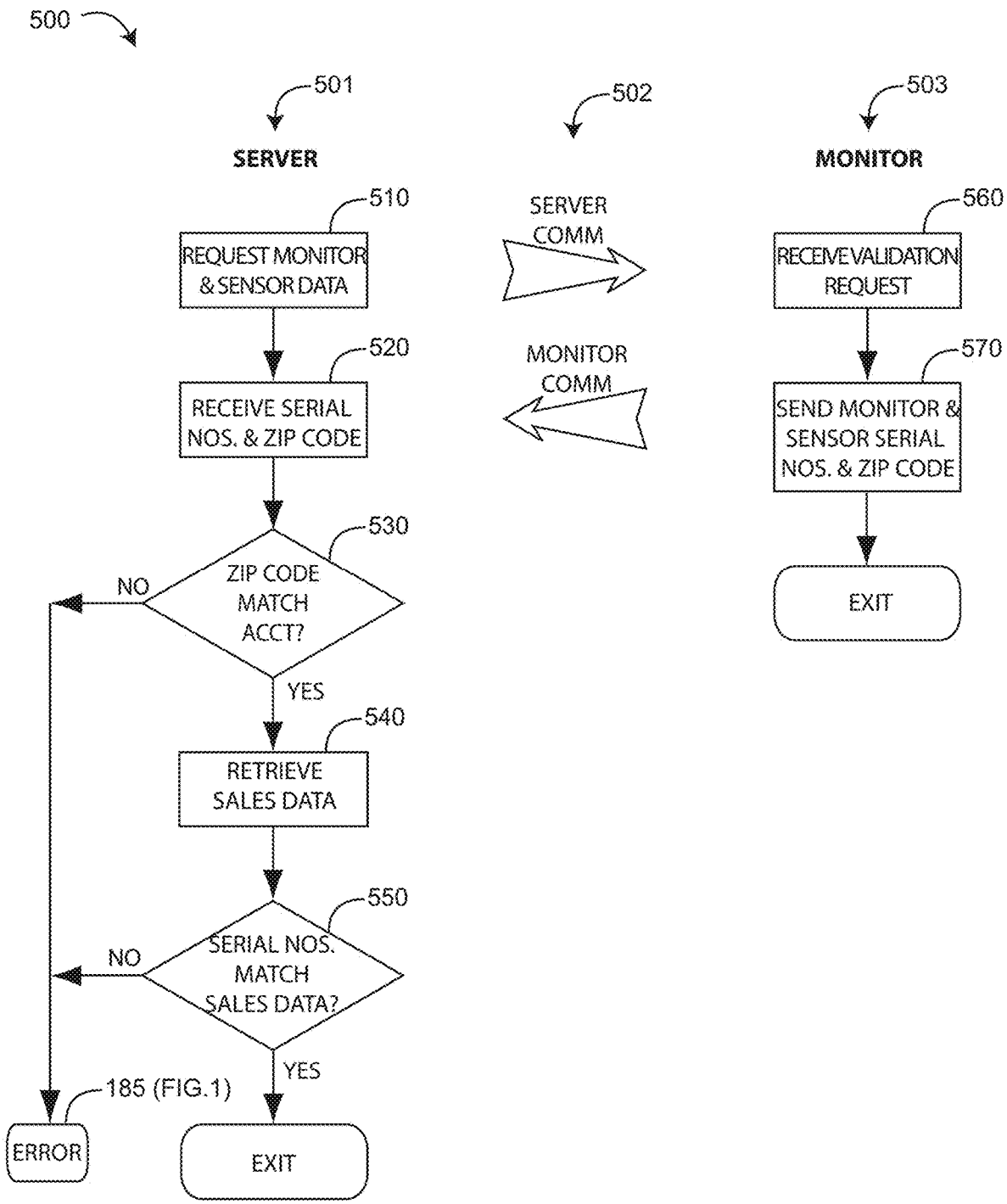
FIG. 5 is a flowchart of server and monitor account validation.

FIG. 5 illustrates monitor and user account validation 500. Validation is performed for direct from manufacturer sales or for sales through distributors. Several validation methods can be used. Monitor and a sensor serial numbers can be compared with sales order records or with tracing data from distributors. A zip code can be used in a manner similar to a credit card, i.e. to prevent a user from accessing a wrong account due to incorrect recording of serial numbers. An address can be used the same as a zip code, but is more secure. However, an address is prone to user error and free text input is difficult to validate. A web registration can be used for distribution sales or direct acute care sales.

As shown in FIG. 5, the server 501 requests monitor and sensor data 510. The monitor 503 receives the request 530 and complies 570. The server 501 receives the requested data 520, which is compared with server records 530-550 for a match. The server sends an error message 185 (FIG. 1) for a monitor to display 180 (FIG. 1), such as Contact Tech Support, if validation data does not match with sales records.

Figure 6:
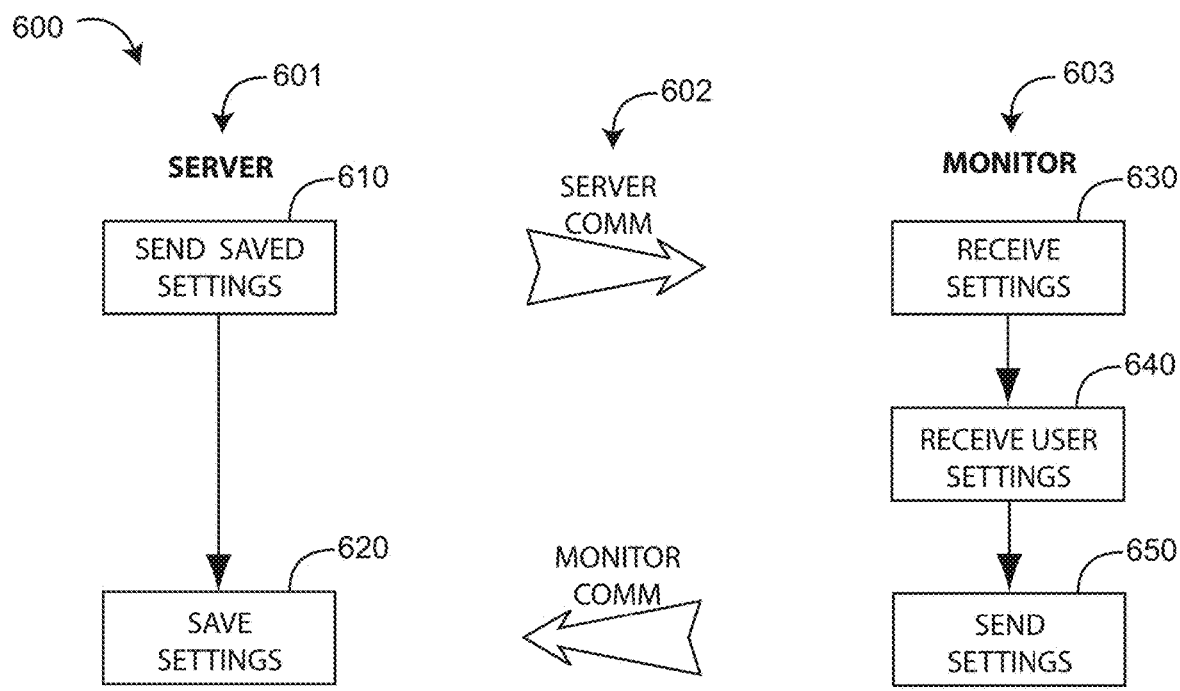
FIG. 6 is a flowchart of a server one-time monitor setup.

FIG. 6 illustrates a server 610 performing a monitor setup 600. The server 601 sends saved settings 610 to the monitor 630. The user can always change settings online 640. The monitor 650 sends these to the server to save 620. Any configuration parameters that the monitor needs to remember, such as the low credit threshold, are saved on the server side 601. The server 601 initially sends a set of commands/queries to the monitor to get configuration parameters (not shown). These parameters include: turn on/off auto-download; define threshold that initiates automatic download; and define number of credits to automatically download. The server may also perform an extra one-time validation, using, e.g., a zip code or the last 4 digits of an account number. If any errors occur on the monitor side, a local message is displayed and the connection is dropped. If any errors occur on server side, the server may choose to display an error message on the server side (via GUI commands) and drop the connection.

Figure 7:
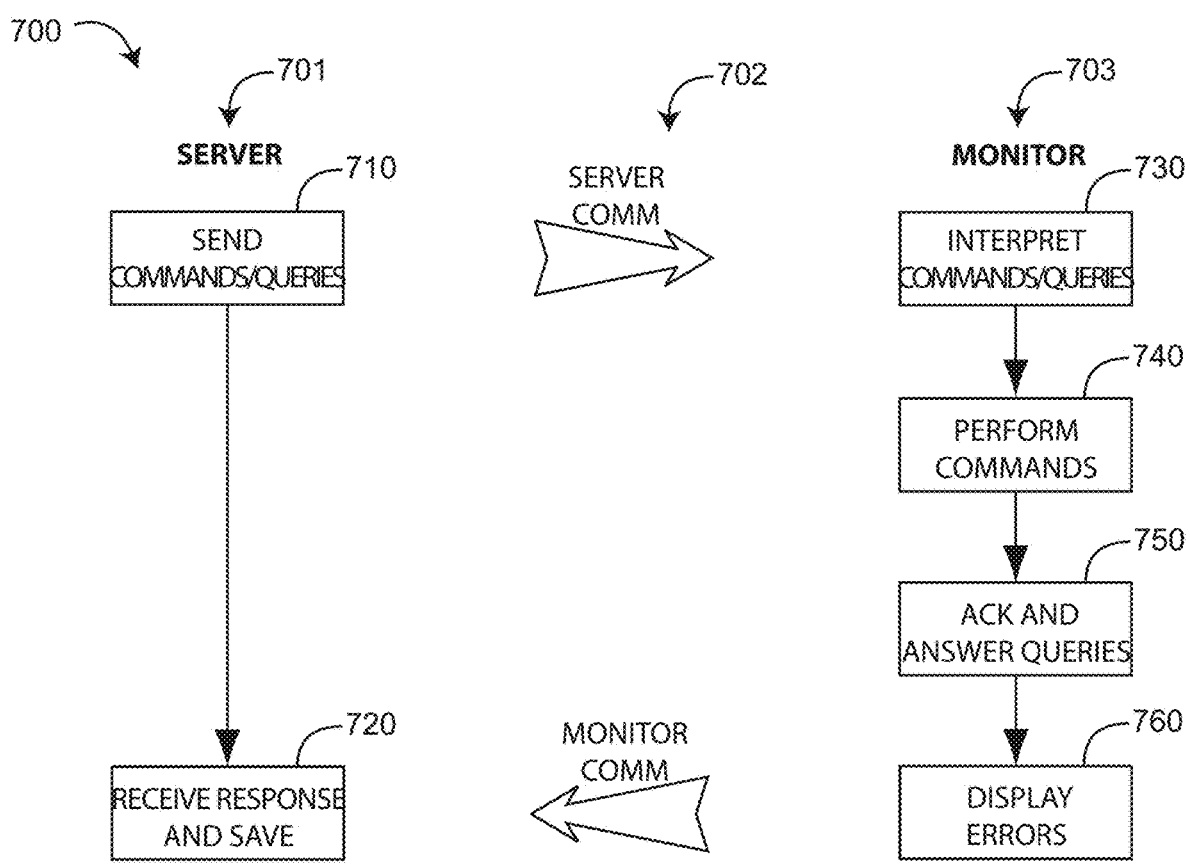
FIG. 7 is a flowchart of server command and monitor acknowledgement communications.

FIG. 7 illustrates server command and monitor acknowledgement communications 700. Once a connection is established, the server assumes the master role and the monitor assumes a slave role. The server 701 sends commands/queries 710, which the monitor 703 interprets 30. The monitor 703 performs the commands 740 and acknowledges/answers the queries 750. Any errors are displayed 760 on the monitor 703. The sensor 701 saves the monitor responses 720. In an embodiment, the server sends commands in a form of HTML-like NMEA data.

Figure 8A:
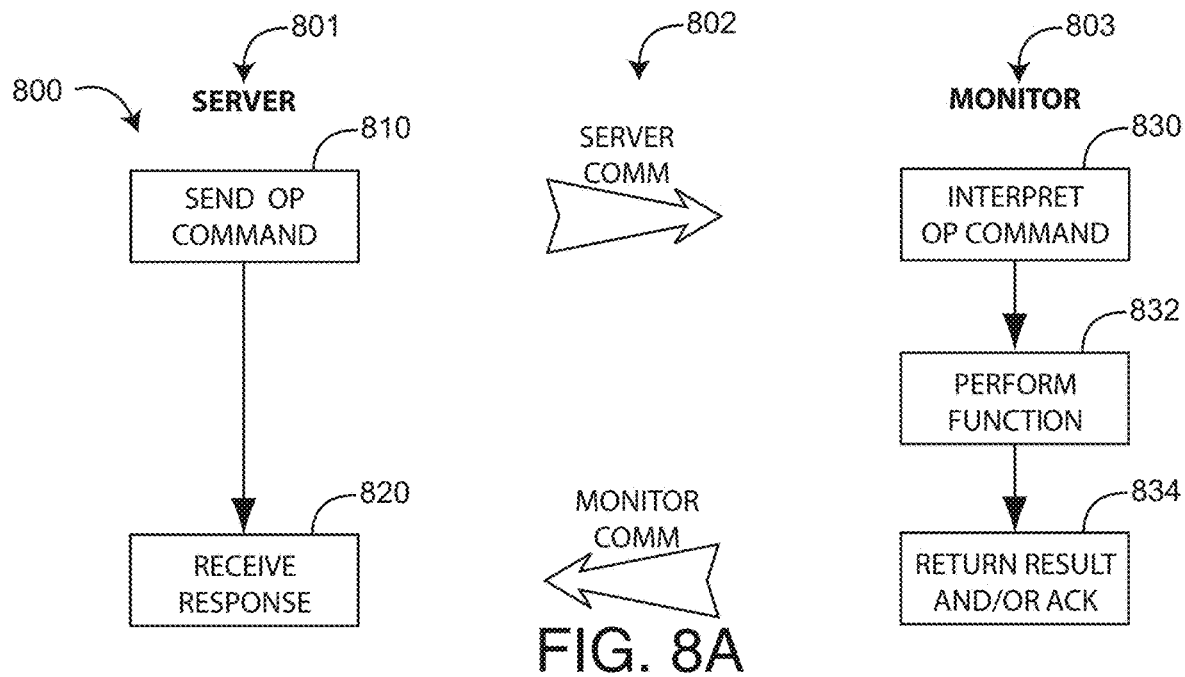
FIGS. 8A-C are flowcharts of server communications of and monitor responses to operational, GUI and hybrid commands.
Figure 8B:
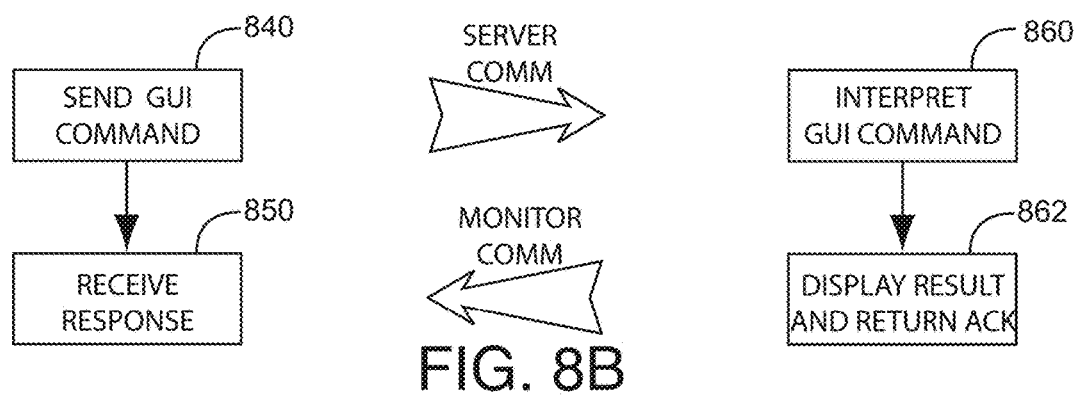
Figure 8C:
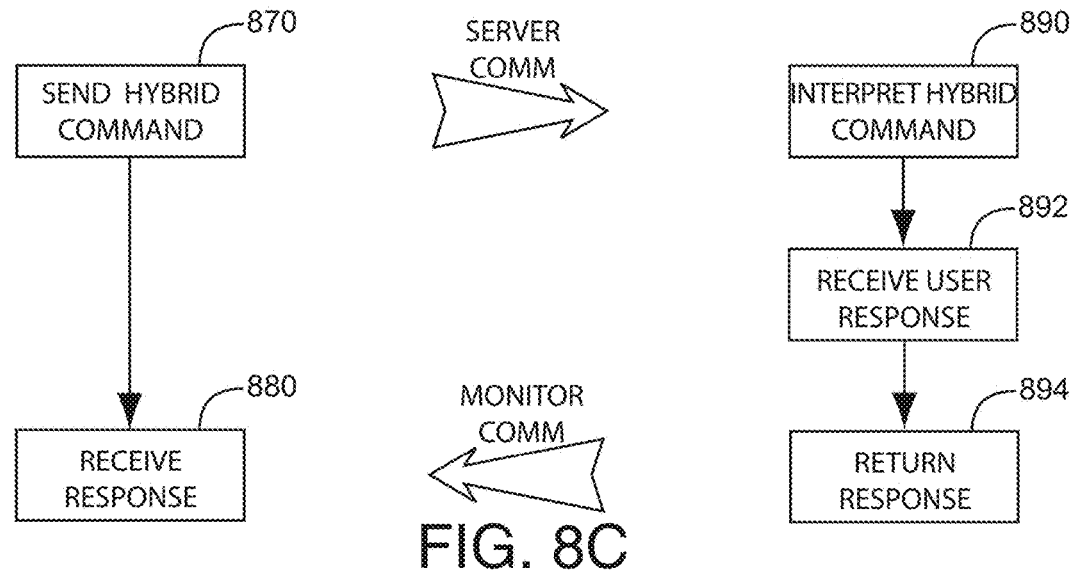

FIGS. 8A-C illustrate server commands and monitor responses to those commands. The server 801 may send three types of commands including an operational command 810, a GUI command 840 and a hybrid command 870. For example, an operational command 810 may be "get zip code," or "accept credit file and send back ACK." GUI commands 840 may be, for example, display message "online credit update in progress." A hybrid command 870 may be to display a GUI as well as expect a response from the monitor user. An example would be a command to display the message "want to turn on auto update?" and wait for a "yes" or "no" response.

As shown in FIGS. 8A-C, the monitor 803 response to an op command 830 is to perform a function 832 and return a result and/or ACK 834. The monitor 803 response to a GUI command 860 is to display a result and ACK 862. The monitor 803 response to a hybrid command 890 is to receive and return a user response 892, 894.

A physiological test credit method has been disclosed in detail in connection with various embodiments. These embodiments are disclosed by way of examples only and are not to limit the scope of the claims that follow. One of ordinary skill in art will appreciate many variations and modifications.

What is claimed is:

1. A physiological monitoring system configured to perform parameter spot-checks on a per test credit basis, the physiological monitoring system comprising:
  a sensor configured to be placed at a measurement location of a user, the sensor comprising a memory configured to store one or more test credits;
  a physiological monitor configured to be coupled to the sensor and comprising one or more signal processors;
  wherein, when enabled by one of the one or more test credits stored in the memory of the sensor, the one or more signal processors of the physiological monitor are configured to receive and process signals that are outputted by the sensor to make a physiological measurement of the user, a number of the one or more test credits stored in the memory of the sensor decremented after each physiological measurement, and
  wherein the physiological monitor is configured to initiate communication with a server in response to the number of the one or more test credits stored in the memory of the sensor falling below a predetermined threshold by securely connecting to the server, wherein:
    upon a pairing between the physiological monitor and/or a user account and a correct manufacturer or distributor having been validated based at least in part on the physiological monitor sending monitor and/or sensor data to the server to be matched to sales records of manufacturers or distributors, the physiological monitor transfers additional test credits received from the server to the memory of the sensor, and
    the server updates the user account to reflect that the additional test credits have been downloaded by the physiological monitor from the server.

2. The physiological monitoring system of claim 1, wherein the physiological monitor is configured to initiate communication with the server by:
  receiving the additional test credits from the server, and
  sending an acknowledgement for receipt of the additional test credits to the server.

3. The physiological monitoring system of claim 2, wherein the physiological monitor performs a hand-shake with the server upon the server receiving the acknowledgement.

4. The physiological monitoring system of claim 2, wherein the physiological monitor securely connecting to the server comprises the physiological monitor exchanging challenges with the server.

5. The physiological monitoring system of claim 1, wherein the additional test credits comprises a user-predefined download quantum of the one or more test credits.

6. The physiological monitoring system of claim 5, wherein the physiological monitor is configured to automatically adjust the user-predefined download quantum and/or the predetermined threshold according to a frequency of test credit usage or a frequency of test credit downloads.

7. The physiological monitoring system of claim 1, wherein the server updating the user account comprises the server deducting the additional test credits from the user account and incrementing a test credit downloading index count.

8. The physiological monitoring system of claim 1, wherein the physiological monitor is configured to determine the number of the one or more test credits stored in the memory of the sensor after each physiological measurement.

9. The physiological monitoring system of claim 1, wherein the sensor comprises an optical sensor configured to transmit optical radiation at a plurality of wavelengths.

10. The physiological monitoring system of claim 1, wherein the physiological monitor is configured to send monitor and/or sensor data to the server to be matched to sales records of manufacturers or distributors to validate the pairing between the physiological monitor and/or the user account and the correct manufacturer or distributor each time the physiological monitor initiates communication with the server or one time prior to initiating a first communication with the server.

11. A physiological test credit system configured to enable a physiological monitor to perform parameter spot-checks, the system comprising:
  a physiological monitor configured to be coupled to a physiological sensor, the physiological monitor comprising one or more signal processors,
  wherein, when enabled by a test credit stored in a memory of the physiological sensor, the physiological monitor is configured to receive and process signals outputted by the physiological sensor to make a physiological measurement of a user, the physiological monitor decrementing a number of test credits stored in the memory of the physiological sensor after each physiological measurement,
  wherein the physiological monitor is configured to initiate communication with a server in response to the number of test credits stored in the memory of the physiological sensor falling below a predetermined threshold, and
  wherein, upon the physiological monitor having been securely connected to the server and a pairing between the physiological monitor and/or a user account and a correct manufacturer or distributor having been validated based at least in part on the physiological monitor sending monitor and/or sensor data to the server to be matched to sales records of manufacturers or distributors, the physiological monitor is configured to update the number of the test credits stored in the memory of the physiological sensor and the server is configured to update the user account to reflect that additional test credits have been downloaded by the physiological monitor from the server.

12. The physiological test credit system of claim 11, wherein the physiological monitor is configured to securely connect to the server by:
  processing server commands instructing the physiological monitor to download the additional test credits from the server,
  downloading the additional test credits from the server, and
  sending an acknowledgement for receipt of the additional test credits to the server.

13. The physiological test credit system of claim 12, wherein the physiological monitor is configured to perform a hand-shake with the server upon the server receiving the acknowledgement.

14. The physiological test credit system of claim 11, wherein the physiological monitor securely connecting to the server comprises the physiological monitor exchanging challenges with the server.

15. The physiological test credit system of claim 14, wherein the physiological monitor exchanges challenges with the server by:
  receiving a server challenge code sent from the server;
  breaking the server challenge code; and
  sending a monitor challenge code to the server for the server to break the monitor challenge code.

16. The physiological test credit system of claim 11, wherein the server updating the user account comprises the server deducting the additional test credits from the user account and incrementing a test credit downloading index count.

17. The physiological test credit system of claim 11, wherein the additional test credits comprise a user-predefined download quantum of test credits.

18. The physiological test credit system of claim 17, wherein the physiological monitor is configured to automatically adjust the user-predefined download quantum and/or the predetermined threshold according to a frequency of test credit usage or to a frequency of test credit downloads.

19. The physiological test credit system of claim 11, wherein the physiological monitor is configured to determine the number of test credits stored in the memory of the physiological sensor after each physiological measurement.

20. The physiological test credit system of claim 11, wherein the physiological monitor is configured to send monitor and/or sensor data to the server to be matched to sales records of manufacturers or distributors to validate the pairing between the physiological monitor and/or the user account and the correct manufacturer or distributor each time the physiological monitor initiates communication with the server or one time prior to initiating a first communication with the server.

* * * * *